(12) United States Patent
Railkar et al.

(10) Patent No.: US 12,036,224 B2
(45) Date of Patent: Jul. 16, 2024

(54) FORMULATIONS, METHODS, KITS, AND DOSAGE FORMS FOR TREATING ATOPIC DERMATITIS AND FOR IMPROVED STABILITY OF AN ACTIVE PHARMACEUTICAL INGREDIENT

(71) Applicant: Libertas Bio, Inc., Lawrenceville, NJ (US)

(72) Inventors: Aruna Railkar, Wayne, NJ (US); Paras Jariwala, Somerset, NJ (US); Wantanee Phuapradit, Montville, NJ (US); David Zammit, Fort Lee, NJ (US); Louis Denis, Princeton, NJ (US); Niranjan Rao, Montgomery, NJ (US); Helen Usansky, Hillsborough, NJ (US); Sandeep Gupta, Plainsboro, NJ (US)

(73) Assignee: Libertas Bio, Inc., New York, NY (US)

( * ) Notice: Subject to any disclaimer, the term of this patent is extended or adjusted under 35 U.S.C. 154(b) by 0 days.

(21) Appl. No.: 18/167,123

(22) Filed: Feb. 10, 2023

(65) Prior Publication Data

US 2023/0270746 A1    Aug. 31, 2023

Related U.S. Application Data

(63) Continuation of application No. 15/966,436, filed on Apr. 30, 2018, now abandoned.

(60) Provisional application No. 62/630,392, filed on Feb. 14, 2018, provisional application No. 62/514,246, filed on Jun. 2, 2017, provisional application No. 62/491,655, filed on Apr. 28, 2017.

(51) Int. Cl.
| | | |
|---|---|---|
| *A61K 31/519* | (2006.01) | |
| *A61K 9/20* | (2006.01) | |
| *A61P 17/00* | (2006.01) | |
| *A61P 37/00* | (2006.01) | |

(52) U.S. Cl.
CPC .......... *A61K 31/519* (2013.01); *A61K 9/2013* (2013.01); *A61K 9/2018* (2013.01); *A61K 9/2054* (2013.01); *A61K 9/2095* (2013.01); *A61P 17/00* (2018.01); *A61P 37/00* (2018.01)

(58) Field of Classification Search
CPC .. A61K 31/519; A61K 9/2054; A61K 9/2095; A61P 17/00
See application file for complete search history.

(56) References Cited

U.S. PATENT DOCUMENTS

| | | | |
|---|---|---|---|
| 3,764,598 A | 10/1973 | Yurugi et al. | |
| 6,764,997 B2 * | 7/2004 | Tenengauzer | ........... A61P 31/04 |
| | | | 536/7.4 |
| 7,037,917 B2 | 5/2006 | De Corte et al. | |
| 7,825,116 B2 | 11/2010 | Singh et al. | |
| 8,729,079 B2 | 5/2014 | Venkatesan et al. | |
| 9,382,277 B2 | 7/2016 | Venkatesan et al. | |
| 10,183,944 B2 | 1/2019 | Venkatesan et al. | |
| 10,188,654 B2 | 1/2019 | Reddy | |
| 10,647,720 B2 | 5/2020 | Venkatesan et al. | |
| 2002/0001617 A1 | 1/2002 | Lee et al. | |
| 2003/0055039 A1 * | 3/2003 | Ikeya | ....................... A61P 29/00 |
| | | | 514/408 |
| 2003/0176369 A1 | 9/2003 | Tenengauzer et al. | |
| 2004/0176400 A1 | 9/2004 | Capelli | |
| 2006/0222671 A1 * | 10/2006 | Weidner | .................. A61P 17/02 |
| | | | 424/401 |
| 2006/0223741 A1 | 10/2006 | Smith | |
| 2007/0066632 A1 | 3/2007 | Hart | |
| 2008/0194656 A1 | 8/2008 | Berwaer | |
| 2009/0181993 A1 | 7/2009 | Guillemont | |
| 2010/0137313 A1 | 6/2010 | Boriack-Sjodin | |
| 2010/0216827 A1 | 8/2010 | Ma | |
| 2011/0111018 A1 * | 5/2011 | Ashraf | ............... A61K 31/4709 |
| | | | 424/452 |
| 2012/0129851 A1 | 5/2012 | Smith | |
| 2014/0038952 A1 | 2/2014 | Smith et al. | |
| 2014/0242063 A1 | 8/2014 | Duffield et al. | |
| 2018/0280304 A1 | 10/2018 | Uramatsu et al. | |

(Continued)

FOREIGN PATENT DOCUMENTS

| | | |
|---|---|---|
| CN | 103974955 A | 8/2014 |
| EP | 1 970 373 A1 | 9/2008 |

(Continued)

OTHER PUBLICATIONS

Markarian (https://www.pharmtech.com/view/using-micronization-reduce-api-particle-size) published Jan. 16, 2013, pp. 1-18 ( Year: 2013).*

Arias-Palomo, E. et al., 3D structure of Syk kinase determined by single particle electron microscopy, Biochim. Biophys. Acta, 1774(12):1493-1499 (2007).

Bhagwat, S. S., Kinase Inhibitors for the Treatment of Inflammatory and Autoimmune Disorders, Puri. Signal., 5:107-115 (2009).

Braselmann, S. et al., R406, an Orally Available Spleen Tyrosine Kinase Inhibitor Blocks Fc Receptor Signaling and Reduces Immune Complex-Mediated Inflammation, Jrnl. Pharm. Exper. Thera., 319(3):998-1008 (2006).

(Continued)

*Primary Examiner* — Andrew S Rosenthal
(74) *Attorney, Agent, or Firm* — Choate, Hall & Stewart LLP; Charles E. Lyon; Michael A. Shinall

(57) ABSTRACT

Embodiments of the disclosure relate generally to formulations, methods of treatment, kits, and dosage forms for treating inflammatory disorders, including topic dermatitis, cancer, the formulations comprising an active pharmaceutical ingredient. The formulation provided comprises granules, wherein the granules comprise: micronized active ingredient; one or more granulation binders; one or more fillers; one or more disintegrants; and one or more antioxidants. In one embodiment, the methods of treatment include orally administering the active ingredient to a subject suffering from atopic dermatitis, where the active ingredient, is in an amount of about 20 mg to about 80 mg.

26 Claims, 26 Drawing Sheets

(56) References Cited

U.S. PATENT DOCUMENTS

| | | |
|---|---|---|
| 2019/0008868 A1 | 1/2019 | Railkar et al. |
| 2019/0070182 A1 | 3/2019 | Reddy |
| 2020/0190095 A1 | 6/2020 | Venkatesan et al. |

FOREIGN PATENT DOCUMENTS

| | | | |
|---|---|---|---|
| JP | S50101387 A | 8/1975 | |
| JP | 2006-528221 A | 12/2006 | |
| JP | 2014-524475 A | 9/2014 | |
| WO | WO-1994/25446 A1 | 11/1994 | |
| WO | WO-1995/19774 A1 | 7/1995 | |
| WO | WO-1995/022325 A1 | 8/1995 | |
| WO | WO-1999/43671 A1 | 9/1999 | |
| WO | WO-2003/075828 A2 | 9/2003 | |
| WO | WO-2004/087053 A2 | 10/2004 | |
| WO | WO-2004/100944 A1 | 11/2004 | |
| WO | WO-2005/012294 A1 | 2/2005 | |
| WO | WO-2006/100310 A1 | 9/2006 | |
| WO | WO-2006/105063 A1 | 10/2006 | |
| WO | WO-2007/082131 A1 | 7/2007 | |
| WO | WO-2007/125405 A2 | 11/2007 | |
| WO | WO-2008/074982 A1 | 6/2008 | |
| WO | WO-2008/112913 A1 | 9/2008 | |
| WO | WO-2009/097287 A1 | 8/2009 | |
| WO | WO-2009/099801 A1 | 8/2009 | |
| WO | WO-2010/038060 A1 | 4/2010 | |
| WO | WO-2011/053861 A1 | 5/2011 | |
| WO | WO-2011/079105 A1 | 6/2011 | |
| WO | WO-2013/028818 A1 | 2/2013 | |
| WO | WO-2013028818 A1 * | 2/2013 | ........... A61K 31/519 |
| WO | WO-2017/095898 A1 | 6/2017 | |
| WO | WO-2018/201131 A1 | 11/2018 | |

OTHER PUBLICATIONS

Gans, E. H. et al., The Use of Polyethylene Glycol in Tablet Coating, Jrnl. Amer Pharm. Assoc., 43(8):483-485 (1954).

Ghoreschi, K. et al., Selectivity and therapeutic inhibition of kinases: to be or not to be?, Nature Immun., 10(4):356-360 (2009).

International Search Report for PCT/US2018/030158, 2 pages (mailed Aug. 1, 2018).

Kontzias, A. et al., Kinase Inhibitors in the Treatment of Immune-Mediated Disease, F1000, Repo. Med., 1-8 (2012).

Law, C-L et al., Molecular Cloning of Human Syk, J.Biol. Chem., 269 (16):12310-12319 (1994).

Mavers, M. et al., Intracellular Signal Pathways: Potential for Therapies, Curr. Rheumatoal Rep., 11(5):378-385 (2009).

Moore, W. J. et al., An analysis of the diaminopyrimidine patent estates describing spleen tyrosine kinase inhibitors by Rigel and Portola, Expert Opin. Ther. Patents, 20(12):1703-1722 (2010).

O'Shea, J. J. et al., The JAK-STAT Pathway: Impact on Human Disease and Therapeutic Intervention, Ann. Rev. Med., 66:311-328 (2015).

Rodig, S. J. et al., Disruption of the Jak1 Gene Demonstrates Obligatory and Nonredundant Roles of the JAKs in Cytokine-Induced Biologic Responses, Cell, 93(3):373-383 (1998).

Siew, A, Micronization as a Bioavailability Enhancement Tool (2014), <https://www.pharmtech.com/view/micronization-bioavailability-enhancement-tool>.

Tanaka, Y. et al., Jak and Syk: Emerging their relevance to the treatment of inflammatory diseases, Inflammation and Regeneration, 31(3):237-244 (2011).

Villaseñor, A. G. et al., Structural Insights for Design of Potent Spleen Tyrosine Kinase Inhibitors from Crystallographic Analysis of Three Inhibitor Complexes, Chem. Biol. Drug Des., 73:466-470 (2009).

Walker, M. E. et al., New insights into the role of mast cells in autoimmunity: Evidence for a common mechanism of action?, Biochim. Biophys. Acta, 1822:57-65 (2012).

Yamaoka, K. et al., The Janus kinases (Jaks), Genome Bio., 2004, vol. 5(12):253.1-253.6 (2004).

* cited by examiner

| Size (μm) | Volume in % | Size (μm) | Volume in % | Size (μm) | Volume in % | Size (μm) | Volume in % | Size (μm) | Volume in % | Size (μm) | Volume in % |
|---|---|---|---|---|---|---|---|---|---|---|---|
| 0.010 | 0.00 | 0.105 | 0.00 | 1.096 | 0.48 | 11.482 | 7.43 | 120.226 | 0.00 | 1258.925 | 0.00 |
| 0.011 | 0.00 | 0.120 | 0.00 | 1.259 | 0.54 | 13.183 | 7.38 | 138.083 | 0.00 | 1445.440 | 0.00 |
| 0.013 | 0.00 | 0.138 | 0.00 | 1.445 | 0.60 | 15.136 | 7.00 | 158.489 | 0.00 | 1659.587 | 0.00 |
| 0.015 | 0.00 | 0.158 | 0.00 | 1.660 | 0.67 | 17.378 | 6.36 | 181.970 | 0.00 | 1905.461 | 0.00 |
| 0.017 | 0.00 | 0.182 | 0.00 | 1.905 | 0.75 | 19.953 | 5.58 | 208.930 | 0.00 | 2187.762 | 0.00 |
| 0.020 | 0.00 | 0.209 | 0.02 | 2.188 | 0.84 | 22.909 | 4.69 | 239.883 | 0.00 | 2511.886 | 0.00 |
| 0.023 | 0.00 | 0.240 | 0.08 | 2.512 | 0.97 | 26.303 | 3.85 | 275.423 | 0.00 | 2884.032 | 0.00 |
| 0.026 | 0.00 | 0.275 | 0.11 | 2.884 | 1.18 | 30.200 | 3.10 | 316.228 | 0.00 | 3311.311 | 0.00 |
| 0.030 | 0.00 | 0.316 | 0.15 | 3.311 | 1.45 | 34.674 | 2.47 | 363.078 | 0.00 | 3801.894 | 0.00 |
| 0.035 | 0.00 | 0.363 | 0.18 | 3.802 | 1.87 | 39.811 | 1.95 | 416.869 | 0.00 | 4365.158 | 0.00 |
| 0.040 | 0.00 | 0.417 | 0.21 | 4.365 | 2.44 | 45.709 | 1.53 | 478.630 | 0.00 | 5011.872 | 0.00 |
| 0.046 | 0.00 | 0.479 | 0.24 | 5.012 | 3.15 | 52.481 | 1.19 | 549.541 | 0.00 | 5754.399 | 0.00 |
| 0.052 | 0.00 | 0.550 | 0.27 | 5.754 | 4.00 | 60.256 | 0.84 | 630.957 | 0.00 | 6606.934 | 0.00 |
| 0.060 | 0.00 | 0.631 | 0.30 | 6.607 | 4.91 | 69.183 | 0.54 | 724.436 | 0.00 | 7585.776 | 0.00 |
| 0.069 | 0.00 | 0.724 | 0.33 | 7.586 | 5.81 | 79.433 | 0.26 | 831.764 | 0.00 | 8709.636 | 0.00 |
| 0.079 | 0.00 | 0.832 | 0.37 | 8.710 | 6.58 | 91.201 | 0.06 | 954.993 | 0.00 | 10000.000 | 0.00 |
| 0.091 | 0.00 | 0.858 | 0.42 | 10.000 | 7.16 | 104.713 | 0.00 | 1096.478 | 0.00 | | |
| 0.105 | 0.00 | 1.096 | | 11.482 | | 120.226 | | 1258.925 | | | |

Operator notes: For Information Only, RUN IN HEXANE

FIG. 1 (continued)

| Size (µm) | Volume in % | Size (µm) | Volume in % | Size (µm) | Volume in % | Size (µm) | Volume in % | Size (µm) | Volume in % |
|---|---|---|---|---|---|---|---|---|---|
| 0.010 | 0.00 | 0.105 | 0.00 | 1.096 | 1.08 | 11.482 | 6.95 | 120.226 | 0.00 | 1258.925 | 0.00 |
| 0.011 | 0.00 | 0.120 | 0.00 | 1.259 | 1.08 | 13.183 | 5.28 | 138.063 | 0.00 | 1445.440 | 0.00 |
| 0.013 | 0.00 | 0.138 | 0.00 | 1.445 | 1.08 | 15.136 | 3.55 | 158.489 | 0.00 | 1659.587 | 0.00 |
| 0.015 | 0.00 | 0.158 | 0.00 | 1.660 | 1.07 | 17.378 | 1.73 | 181.970 | 0.00 | 1905.461 | 0.00 |
| 0.017 | 0.00 | 0.182 | 0.00 | 1.905 | 1.09 | 19.953 | 0.51 | 208.930 | 0.00 | 2187.762 | 0.00 |
| 0.020 | 0.00 | 0.209 | 0.00 | 2.188 | 1.17 | 22.909 | 0.06 | 239.883 | 0.00 | 2511.886 | 0.00 |
| 0.023 | 0.00 | 0.240 | 0.06 | 2.512 | 1.36 | 26.303 | 0.00 | 275.423 | 0.00 | 2884.032 | 0.00 |
| 0.026 | 0.00 | 0.275 | 0.17 | 2.884 | 1.73 | 30.200 | 0.00 | 316.228 | 0.00 | 3311.311 | 0.00 |
| 0.030 | 0.00 | 0.316 | 0.28 | 3.311 | 2.34 | 34.674 | 0.00 | 363.078 | 0.00 | 3801.894 | 0.00 |
| 0.035 | 0.00 | 0.363 | 0.39 | 3.802 | 3.21 | 39.811 | 0.00 | 416.869 | 0.00 | 4365.158 | 0.00 |
| 0.040 | 0.00 | 0.417 | 0.52 | 4.365 | 4.33 | 45.709 | 0.00 | 478.630 | 0.00 | 5011.872 | 0.00 |
| 0.046 | 0.00 | 0.479 | 0.64 | 5.012 | 5.63 | 52.481 | 0.00 | 549.541 | 0.00 | 5754.399 | 0.00 |
| 0.052 | 0.00 | 0.550 | 0.75 | 5.754 | 6.98 | 60.256 | 0.00 | 630.957 | 0.00 | 6606.934 | 0.00 |
| 0.060 | 0.00 | 0.631 | 0.86 | 6.607 | 8.19 | 69.183 | 0.00 | 724.436 | 0.00 | 7585.776 | 0.00 |
| 0.069 | 0.00 | 0.724 | 0.95 | 7.586 | 9.06 | 79.433 | 0.00 | 831.764 | 0.00 | 8709.636 | 0.00 |
| 0.079 | 0.00 | 0.832 | 1.02 | 8.710 | 9.42 | 91.201 | 0.00 | 954.993 | 0.00 | 10000.000 | 0.00 |
| 0.091 | 0.00 | 0.858 | 1.06 | 10.000 | 9.18 | 104.713 | 0.00 | 1096.478 | 0.00 | | |
| 0.105 | 0.00 | 1.096 | 1.06 | 11.482 | 8.31 | 120.226 | 0.00 | 1258.925 | 0.00 | | |

Operator notes: Suspended in Hexane with SPAN 85.

Malvern Instruments Ltd.
Malvern, UK
Tel: =+[44] (0) 1684-892456 Fax +[44] (0) 1684-892789

Mastersizer 2000 Ver. 5.60
Serial Number: MAL1012747

File name: 08082014 Lot BPR-13-123-81-11
Record Number: 36
8/20/2014 3:53:11 PM

FIG. 2 (continued)

5-D Pruritus Scale

1. <u>Duration</u>: During the last 2 weeks, how many hours a day have you been itching?

| Less than 6hrs/day | 6-12 hrs/day | 12-18 hrs/day | 18-23 hrs/day | All day |
   |---|---|---|---|---|
   | ☐ | ☐ | ☐ | ☐ | ☐ |
   | 1 | 2 | 3 | 4 | 5 |

2. <u>Degree</u>: Please rate the intensity of your itching over the past 2 weeks

| Not present | Mild | Moderate | Severe | Unbearable |
   |---|---|---|---|---|
   | ☐ | ☐ | ☐ | ☐ | ☐ |
   | 1 | 2 | 3 | 4 | 5 |

3. <u>Direction</u>: Over the past 2 weeks has your itching gotten better or worse compared to the previous month?

| | Completely resolved | Much better, but still present | Little bit better, but still present | Unchanged | Getting worse |
   |---|---|---|---|---|---|
   | Sleep | ☐ | ☐ | ☐ | ☐ | ☐ |
   | | 1 | 2 | 3 | 4 | 5 |

4. <u>Disability</u>: Rate the impact of your itching on the following activities over the last 2 weeks

| | Never affects sleep | Occasionally delays falling asleep | Frequently delays falling asleep | Delays falling asleep and occasionally wakes me up at night | Delays falling asleep and frequently wakes me up at night |
   |---|---|---|---|---|---|
   | Sleep | ☐ | ☐ | ☐ | ☐ | ☐ |
   | | 1 | 2 | 3 | 4 | 5 |

| | N/A | Never affects this activity | Rarely affects this activity | Occasionally affects this activity | Frequently affects this activity | Always affects this activity |
   |---|---|---|---|---|---|---|
   | Leisure/Social | ☐ | ☐ 1 | ☐ 2 | ☐ 3 | ☐ 4 | ☐ 5 |
   | Housework/Errands | ☐ | ☐ 1 | ☐ 2 | ☐ 3 | ☐ 4 | ☐ 5 |
   | Work/School | ☐ | ☐ 1 | ☐ 2 | ☐ 3 | ☐ 4 | ☐ 5 |

5. <u>Distribution</u>: Mark whether itching has been present in the following parts of your body over the last 2 weeks. If a body part is not listed, choose the one that is closest anatomically.

| | Present | | Present |
   |---|---|---|---|
   | Head/Scalp | ☐ | Soles | ☐ |
   | Face | ☐ | Palms | ☐ |
   | Chest | ☐ | Tops of Hands/Fingers | ☐ |
   | Abdomen | ☐ | Forearms | ☐ |
   | Back | ☐ | Upper Arms | ☐ |
   | Buttocks | ☐ | Points of Contact w/ Clothing (e.g. waistband, undergarment) | ☐ |
   | Thighs | ☐ | | |
   | Lower Legs | ☐ | Groin | ☐ |
   | Tops of Feet/Toes | ☐ | | |

FIG. 3

Eczema Area and Severity Index (EASI) Assessment Tool

Four anatomic sites--head, upper extremities, trunk, and lower extremities--are assessed for erythema, induration/infiltration (papules), excoriation, and lichenification as seen on the day of the examination. The severity of each sign is assessed using a 4-point scale (half steps are allowed):

- 0 = none
- 1 = mild
- 2 = moderate
- 3 = severe

The area affected by atopic dermatitis within a given anatomic site is extimated as a percentage of the total area of that anatomic site and assigned a numerical value according to the degree of atopic dermatitis involvement as follows:

- 0 = no involvement
- 1 = <10%
- 2 = 10% to <30%
- 3 = 30% to <50%
- 4 = 50% to <70%
- 5 = 70% to <90%
- 6 = 90% to 100%

The EASI score is obtained by using the formula below:

$$EASI = 0.1\,(E_h + I_h + Ex_h + L_h)\,A_h + 0.2\,(E_u + I_u + Ex_u + L_u)\,A_u + 0.3\,(E_t + I_t + Ex_t + L_t)\,A_t + 0.4\,(E_l + I_l + Ex_l + L_l)\,A_l$$

Where E, I, Ex, L, and A denote erythema, induration, excoriation, lichenification and area, respectively, and h, u, t, and l denote head, upper extrmities, trunk, and lower extremities, respectively.

FIG. 4

Patient Demographics

| Demographic | | Placebo | 20 mg | 40 mg | 80 mg |
|---|---|---|---|---|---|
| Age | Average (y) (range) | 29.9 (21-46) | 38.2 (21-62) | 42.4 (24-67) | 33.1 (18-51) |
| Sex | Female (%) | 67 | 44 | 44 | 44 |
| Race | White (%) | 89 | 67 | 78 | 78 |
| EASI | Average (range) | 21.6 (16.1-33.1) | 28.7 (17.1-58) | 21.3 (16.2-34.2) | 29.0 (16.4-52.8) |
| IGA | Average | 3.1 | 3.3 | 3.1 | 3.5 |
| BSA | Average % (range) | 25.1 (13-45) | 45.3 (24-80) | 31.6 (12-70) | 39.0 (15-96) |
| NRS | Average (NRS≥4) | 6.9 | 6.8 | 7.3 | 7.0 |

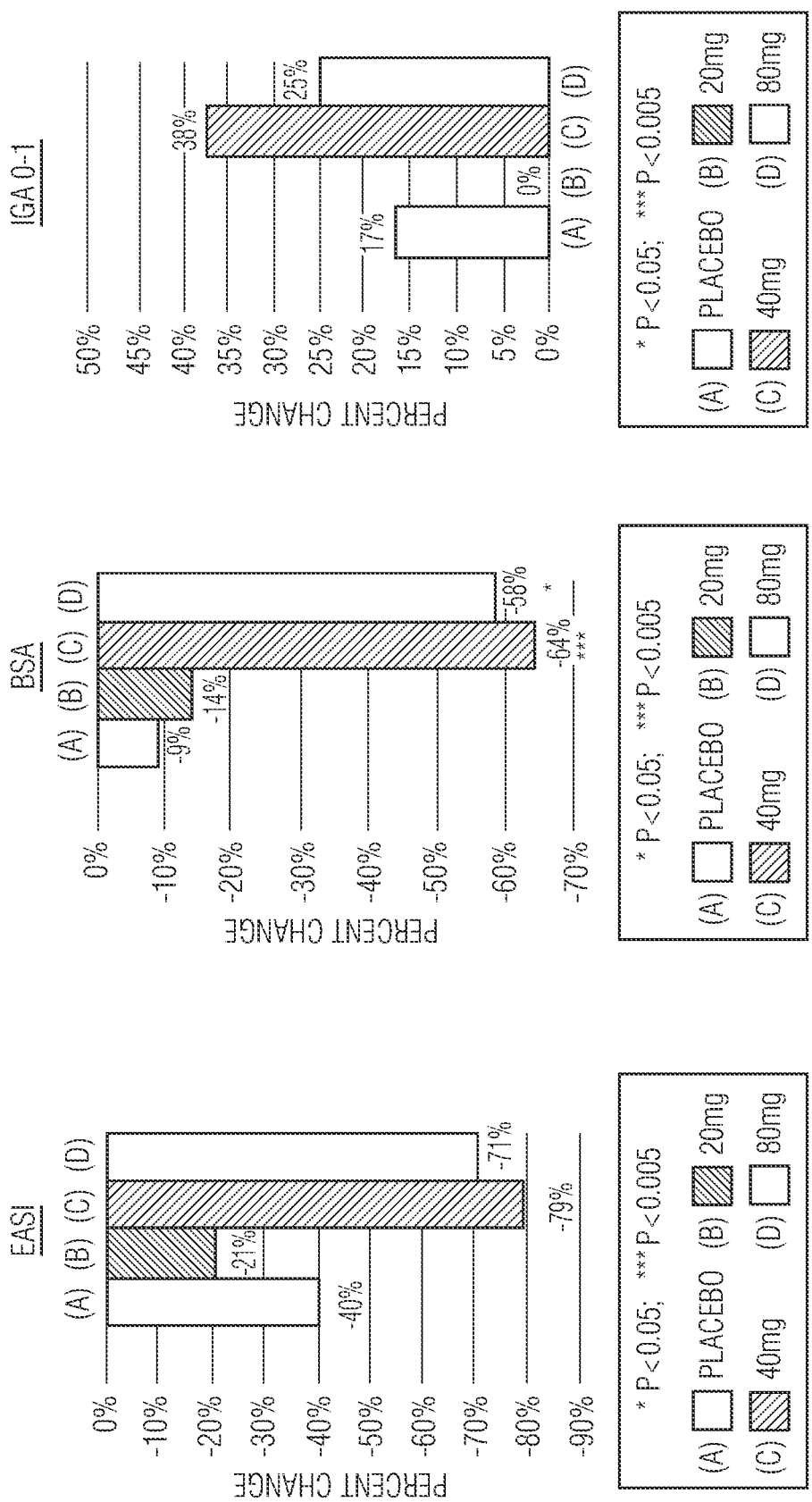

| KINASE | INHIBITION OF KINASE ACTIVITY, IC$_{50}$ (nM) | | | |
|---|---|---|---|---|
| | Cmpd 1 | Tofacitinib | Upadacitinib* | Baricitinib* |
| JAK1 | 46 | 21 | 43 | 5.9 |
| JAK2 | 4 | 7 | 200 | 5.7 |
| JAK3 | 11 | 4 | 2300 | >400 |
| TYK2 | 8 | 3,600 | 4700 | 53 |
| SYK | 5 | >10,000 | NR | NR |

*Literature values

| CYTOKINE | IL-2 | IL-23 | IL-12 | IL-4 | IFN α |
|---|---|---|---|---|---|
| SIGNALING PATHWAY | JAK1, JAK3 | JAK2, TYK2 | JAK2, TYK2 | JAK1, JAK3 | JAK1, TYK2 |
| STAT PHOSPHORYLATION MEASURED | STAT5 | STAT3 | STAT4 | STAT6 | STAT1 |
| IC$_{50}$ (nM)* Cmpd 1 | 87 | 46 | 78 | 352 | 53 |
| Tofacitinib | 32 | 68 | 1040 | 76 | 33 |
| Tamatinib | 242 | 978 | 216 | 2095 | 221 |

*(p<0.001); (p<0.01); *(p<0.05); COMPARED TO BASELINE
+(P<0.1): COMPARED TO PLACEBO

TREATMENT-EMERGENT ADVERSE EVENTS (TEAE)

| SAE (NOT CONSIDERED RELATED) | PLACEBO (n=9) | 20mg (n=9) | 40mg (n=9) | 80mg (n=9) |
|---|---|---|---|---|
| ANXIETY | 0 | 0 | 0 | 1 |
| AE (MORE THAN 5%) | PLACEBO (n=9) | 20mg (n=9) | 40mg (n=9) | 80mg (n=9) |
| HEADACHE | 3 | 1 | 4 | 2 |
| NAUSEA | 2 | 0 | 1 | 2 |
| DIARRHEA | 1 | 0 | 0 | 0 |
| FATIGUE | 0 | 0 | 1 | 1 |
| INCISION SITE INFLAMMATION | 0 | 1 | 0 | 1 |
| HYPERKALIEMIA | 0 | 1 | 0 | 1 |
| BACK PAIN | 0 | 0 | 2 | 0 |
| THROMBOEMBOLIC EVENTS | 0 | 0 | 0 | 0 |
| SERIOUS INFECTIONS | 0 | 0 | 0 | 0 |

Abstracts

Background:
Cmpd 1 is a novel, potent inhibitor of Spleen Tyrosine Kinase (SYK) and Janus Kinases (JAK). Pre-clinical studies indicate that Cmpd1 as low nM $IC_{50}$S against SYK and JAK, decreases proliferation in ibrutinib-resistant cell lines, and suppresses tumor growth in rodent xenograft models of NHL and other hematologic malignancies.

Methods:
This Phase 1/2 clinical trial in patients with solid tumors and hematologic malignancies evaluates escalating Cmpd1 oral doses of 10, 20, 30, 40, 50, and 75 mg BID, and 80 and 120 mg QD mg (NCT02440685). Phase 1 allows patients with solid tumors or hematologic malignancies; Phase 2 allows only patients with diffuse large B-Cell lymphoma (DLBCL), follicular lymphoma (FL) or mantle cell lymphoma (MCL). Endpoints include safety, tolerability, pharmacokinetics, serum markers of inflammation, and response using RECIST or Lugano Classification System.

Results:
Thirty-six patients have enrolled in the DLT phase at doses of 10 mg-100 mg BID and at 80 mg and 120 mg QD. All patients had multiple prior lines of treatment (range: 2-8). Cmpd 1 was well tolerated. No dose limiting adverse events have been reported at these dose levels. Most drug-related adverse events were Gr1/2(e.g. headache, fatigue). Steady-state systemic exposure was high ($C_{max}$,AUC(0-12h) and T1/2 at 75 mg BID were 0.7 µM, 6.3 µM.h and 18 h, respectively). High systemic exposure was also observed at 80 mg QD and 120 mg QD. Robust reduction of CRP, IL-18, MIP1Bβ,VCAM-1, TNFR2 was observed at all doses. Stable disease (RECIST), 9+ months, and 7+ months in patients with peritoneal/ovarian cancer and neuroendocrine pancreatic cancer, respectively, and almost 50% reduction in target lesions at 3 months in a FL patient (Lugano, 6 prior lines) and stable disease and reduction of pruritus in a peripheral T-cell lymphoma patient after 2 months (Lugano, 2 prior lines) of treatment were observed. Accrual of patients continues.

Conclusions:
Cmpd 1 was safe and well tolerated. Encouraging preliminary evidence of efficacy in NHL patients was observed. The dose of 75 mg BID was recommended for Part B of the trial. Dose finding continues for patients with solid tumors.

References
1. C.S. Navara et al., *Curr Pharm Des* 2004, 10: 1739-44
2. J.J. O'Shea et al., *N Eng J Med* 2013, 971: 295-312
3. A. Rosenthal and R.A. Mesa, *Expert Opin Pharmacother* 2014, 15: 1265-76
4. C.U. Niemann and A. Weisner, *Seminars Can Biol* 2013, 23: 410-421
5. J.N. Ihle et al., *Trends Genet* 1995, 11: 69- 74

FIG. 16A

Preclinical Studies

Cmpd 1 Potently Inhibits SYK and JAK Kinases in Biochemical Assays

| Kinase | Inhibition of kinase activity, $IC_{50}$ (nM) | | | |
|---|---|---|---|---|
| | Cmpd 1 | Ruxolitinib | Tofacitinib | Ibrutinib* |
| SYK | 5 | >10,000 | >10,000 | >10,000 |
| JAK1 | 46 | 3 | 21 | NR |
| JAK2 | 4 | 3 | 7 | >10,000 |
| JAK3 | 11 | 390 | 4 | 16 |
| TYK2 | 8 | 20 | 3,600 | NR |

$IC_{50}$ values were determined in biochemical kinase assays using purified partial or full length enzymes. *Literature Values

Cmpd 1 Inhibits Both SYK and JAK Pathways in Mechanistic and Functional Assays in Myeloid Cells

| In vitro Functional Assays | Target | Functional Inhibition $EC_{50}$(nM) | | |
|---|---|---|---|---|
| | | Cmpd1 | Tofacitinib | Tamatinib |
| IgE-immune complex-induced degranulation (hexosaminidase release) by FcRε* rat basophilic leukemia cells, RBL-2H3 | SYK | 14 | >1,000 | 47 |
| IgE-immune complex-induced tyrosine phosphorylation of LAT (a substrate of syk) in FcRε* RBL-2H3 cells | SYK | 143 | NT | 162 |
| IL-6-induced tryosine phosphorylation of STAT3 in THP1 cells | JAK | 70 | 26 | 1,900 |

Cmpd 1 had similar efficacy to tofacitinib and tamatinib in human monocytic leukemic cells, THP1 using an IgG1-immune complex-induced/FcRg+ TNF-$\varepsilon_\alpha$ release assay FIG. 16A (continued)

Cmpd 1 Shows Strong Anti-Proliferative Activity in Lymphoma Cell Lines

| Cell Line | Lymphoma Type | Anti-proliferative Activity (IC$_{50}$, µM) | | |
|---|---|---|---|---|
| | | Cmpd 1 | Ibrutinib* | Ruxolitinib* |
| OCI-LY-10 | DLBCL (ABC) | 0.18 | 0.1 | 16.1 |
| SU-DHL6 | DLBCL (GCB) | 0.36 | 0.18 | NA |
| SU-DHL4 | DLBCL (GCB) | 1.1 | 0.53 | NA |
| OCI-LY-3 | DLBCL (ABC) | >10 | 0>10 | 30 |
| Ramos | Burkitt's | 0.26 | 5.5 | NA |

*Literature values. NA = Not Available

Cmpd 1 Retains Strong Anti-Proliferative Activity in Ibrutinib-Resistant Lymphoma Cells

| Cell Line | Fold Change in IC$_{50}$ (Parental vs Resistant) | |
|---|---|---|
| | Cmpd 1 | Ibrutinib |
| Pool | 1.2 | 27 |
| Clone 1 | 1.9 | 22 |
| Clone 2 | 1.0 | 16 |
| Clone 3 | 0.7 | 17 |
| Clone 4 | 1.4 | 23 |
| Clone 5 | 0.7 | 23 |

FIG. 16A (continued)

CLINICAL TRIAL DATA
DEMOGRAPHICS

| ASSESSMENT | STATISTIC | COHORTS | | | | | | | | |
|---|---|---|---|---|---|---|---|---|---|---|
| | | 10mg BID | 20mg BID | 30mg BID | 40mg BID | 50mg BID | 75mg BID | 100mg BID | 80mg BID | 120mg BID |
| AGE (YRS) | N | 3 | 4 | 3 | 4 | 7 | 6 | 3 | 7 | 3 |
| | MEAN | 65 | 67.5 | 66.3 | 62 | 62.9 | 62.7 | 64 | 65.6 | 74 |
| | MIN, MAX | 44, 82 | 55, 77 | 60, 70 | 53, 69 | 18, 77 | 46, 72 | 43, 78 | 52, 84 | 67, 81 |
| No. OF PRIOR LINES | NHL PATIENTS | N/A | 2 | N/A | 2-7 | 2-3 | 2-7 | 2-9 | 2-4 | 6 |
| | SOLID TUMOR | 2-4 | 2-6 | 2-6 | 3 | 2-3 | 2-5 | 7 | 3-6 | 4-7 |

MEAN PHARMACOKINETIC PARAMETERS OF Cmpd 1 DAY 15

| DOSE LEVEL | $C_{max}$ nM | $AUC_{(0-24h)}$ nM.h* | $C_{trough}$ nM | ACCUMULATION RATIO |
|---|---|---|---|---|
| 10 BID | 216 | 3774 | 125 | 3.0 |
| 20 mg BID | 219 | 2939 | 82 | 2.0 |
| 30 mg BID | 526 | 8576 | 274 | 2.4 |
| 40 mg BID | 728 | 12060 | 457 | 3.0 |
| 50 mg BID | 618 | 9320 | 425 | 2.4 |
| 75 mg BID | 991 | 153646 | 575 | 3.1 |
| 100 mg BID** | 1126 | 17186 | 746 | 2.9 |
| 80 mg QD | 681 | 7108 | 143 | 1.5 |
| 120 mg QD | 1074 | 13280 | 379 | 1.6 |

* AUC(0-24) FOR BID REGIMENS ARE ESTIMATED AS 2 x AUC(0-12)
** n=1

FIG. 16C

CLINICAL TRIAL DATA

Cmpd1 EVIDENCE OF EFFICACY

LYMPHOMA:
- EARLY SIGNS OF CLINICAL ACTIVITY IN NHL PATIENTS WITH MULTIPLE PRIOR LINES (2-6) OF TREATMENT
    - FOLLICULAR LYMPHOMA: 43% REGRESSION OF LYMPH NODES (6+ MONTHS, ONGOING)
    - PERIPHERAL T-CELL LYMPHOMA: SIGNIFICANT SYMPTOMATIC IMPROVEMENT OF PRURITUS AND SKIN INDURATION ASSOCIATED WITH REGRESSION OF LYMPH NODES (5 MONTHS) AND STABLE DISEASE

SOLID TUMORS:
- STABLE DISEASE
    - 9+ MONTHS IN PERITONEAL/OVARIAN CANCER PATIENT
    - 7+ MONTHS IN NEUROENDOCRINE PANCREATIC CANCER PATIENT

SAFETY/TOLERABILITY PROFILE
ADVERSE EVENTS OCCURING IN ≥ 10% OF PATIENTS

| AE TERM | TREATMENT-RELATED ADVERSE REACTIONS | | ANY TREATMENT-EMERGENT ADVERSE EVENTS | |
|---|---|---|---|---|
| GRADE | 1-2 | 3+ | ANY | % |
| ANEMIA | 5 | 1 | 12 | 30% |
| INFECTION | 1 | 1* | 12 | 30% |
| FATIGUE | 6 | 0 | 10 | 25% |
| CONSTIPATION | 2 | 0 | 8 | 20% |
| DIARRHEA | 3 | 0 | 8 | 20% |
| COUGH | 0 | 0 | 7 | 17% |
| FEVER | 2 | 0 | 7 | 17% |
| CHILLS | 1 | 0 | 6 | 15% |
| ABDOMINAL PAIN | 0 | 0 | 5 | 13% |
| ANXIETY | 0 | 0 | 5 | 13% |
| DEHYDRATION | 0 | 0 | 5 | 13% |
| EDEMA | 1 | 0 | 5 | 13% |
| HEADACHE | 4 | 0 | 5 | 13% |
| ACUTE KIDNEY INJURY | 0 | 0 | 4 | 10% |

* DLT: PNEUMONIA IN A PATIENT DOSED AT 100mg BID

RELEVANT LABORATORY ABNORMALITIES:
- NEUROTROPENIA GRADE 3-4 OBSERVED IN 4 SUBJECTS AT DOSES ≥ 80mg TOTAL DAILY DOSE
- THROMBOCYTOPENIA GRADE 3-4 OBSERVED IN 6 SUBJECTS AT DOSES ≥ 80mg TOTAL DAILY DOSE

FIG. 16G

CONCLUSION

- Cmpd1 IS A POTENT DUAL INHIBITOR OF SYK AND JAK KINASES
- Cmpd1 SHOWS ACTIVITY IN A BROAD PANEL OF LYMPHONA/LEUKEMIA CELL LINES, INCLUDING IBRUTINIB RESISTANT CELL LINES
- CLINICAL ACTIVITIES WAS OBSERVED AT DOSES OF 80 mg QD AND 75 mg BID IN HEAVILY PRE-TREATED NHL PATIENTS
- ADVERSE EVENTS ARE CONSISTENT WITH THE MECHANISM, REVERSIBLE AND MANAGEABLE
  - 1 DLT AT 100 mg BID: PNEUMONIA
  - DRUG-RELATED ADVERSE REACTIONS (DRAEs) REPORTED ARE MOSTLY MILD OR MODERATE (CTC GRADE 1-2)
  - ANEMIA AND FATIGUE ARE THE MOST FREQUENTLY REPORTED DRAEs
  - 75mg BID PROVIDES EXCELLENT SYSTEMIC EXPOSURE AND INHIBITION OF INFLAMMATION MARKERS
- 75 mg BID IS RECOMMENDED FOR FURTHER EVALUATION IN HEME MALIGNANCIES
  - PHASE 2 PART HAS BEEN INITIATED IN DLBCL, FL AND MCL
  - PHASE 2 PART IS EXPANDED TO INCLUDE PERIPHERAL T-CELL LYMPHOMA, CHRONIC LYMPHOCYTIC LEUKEMIA AND MYELOFIBROSIS PATIENTS IN ADDITIONAL COHORTS

FIG. 16G (continued)

FORMULATIONS, METHODS, KITS, AND DOSAGE FORMS FOR TREATING ATOPIC DERMATITIS AND FOR IMPROVED STABILITY OF AN ACTIVE PHARMACEUTICAL INGREDIENT

This application is a continuation of U.S. application Ser. No. 15/966,436, filed Apr. 30, 2018, which claims priority to and benefit of U.S. Application No. 62/491,655, filed Apr. 28, 2017, U.S. Application No. 62/514,246, filed Jun. 2, 2017, and U.S. Application No. 62/630,392, filed Feb. 14, 2018, the entire contents of each of which are hereby incorporated by reference.

TECHNICAL FIELD

Embodiments of the disclosure relate generally to formulations, methods, kits, and dosage forms for treating atopic dermatitis and for improved stability of an active pharmaceutical ingredient. In one embodiment, the formulations, methods, kits and dosage forms comprise administering the active pharmaceutical ingredient with improved stability and can be used for the treatment of inflammatory disorders or cancers, or for the treatment of atopic dermatitis.

BACKGROUND

Protein kinases constitute a large family of structurally related enzymes that are responsible for the control of a variety of signal transduction processes within cells. Almost all kinases contain a similar 250 to 300 amino acid catalytic domain. The kinases can be categorized into families by the substrates they phosphorylate.

JAK (Janus kinase, including JAK1, JAK2, JAK3 and TYK2) is a family of intracellular non-receptor tyrosine kinases. JAK is expressed in hematopoietic cells and abundantly in primary leukemic cells from children with acute lymphoblastic leukemia. The downstream substrates of JAK include the signal tranducer activator of transcription (STAT) proteins. STAT proteins function both as signaling molecules and transcription factors and ultimately bind to specific DNA sequences present in the promoters of cytokine-responsive genes. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Spleen tyrosine kinase (syk) is a member of the syk family of protein tyrosine kinases and plays a crucial role in inflammatory and allergic responses. Syk triggers IgE and IgG receptor mediated signaling in mast cells, basophils, and macrophages leading to degranulation and cytokine release.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, and Fc receptors in immune cells and at GPVI and FcγRIIa in platelets to downstream intracellular molecules such as Syk.

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact. The interaction of Syk with diphosphorylated ITAM sequences induces a conformation change in the kinases that allows for tyrosine phosphorylation of the kinase itself.

Not only do these kinases contribute to normal host defense, they also play roles in the pathogenesis of diseases. Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, Alzheimer's disease and hormone-related diseases. As a consequence, there have been substantial efforts in medicinal chemistry to find inhibitors of protein kinases for use as therapeutic agents. There is a need in the art for compounds that are dual inhibitors of Syk/JAK, as well as for methods for treating conditions that can benefit from such inhibition. There is also a need in the art for formulations of compounds that are dual inhibitors of Syk/JAK, that may be utilized in methods for treating conditions that can benefit from such inhibition. Such formulations should optimize the efficacy of Syk/JAK dual inhibitor compounds and should exhibit high levels of stability.

Atopic dermatitis (AD) is a chronic inflammatory skin disease. It is characterized by dry scaly skin, erythema, lesions with oozing and crusting, excoriations due to itch, and lichenification. The skin conditions are accompanied by intense pruritus that poses a significant burden to subjects and their quality of life. Up to 3% of adults have atopic dermatitis and between 15-25% of children. Onset is in early childhood in approximately 85% of cases but onset can occur later including during adulthood.

Spleen tyrosine kinase (SYK) and Janus kinase (JAK) are tyrosine kinases that play important roles in the pathogenesis of various types of autoimmune and inflammatory diseases, including atopic dermatitis. Deregulation of SYK has been implicated in different human diseases such as B-cell malignancies, allergy, asthma, and other inflammatory disorders. SYK binds to the immune-receptor tyrosine-based activation motif (ITAM) present in Fcγ-activating receptors and integrins. Binding of SYK to the ITAM activates downstream signaling events such as activation of Bruton tyrosine kinase (BTK), eventually leading to increased release of cytokines, lipid mediators and various proteases. These mediators cause hyper-proliferation of B-cells, inflammation, and tissue or cartilage damage. SYK also plays a critical role in IL-17R signaling in keratinocytes. Therefore, inhibition of SYK activity provides a potential approach for the treatment of various types of lymphomas and inflammatory disorders.

The JAK kinases (JAK1, JAK2, JAK3 and TYK2) are required for the physiologic signaling through the cytokines and growth factor receptors that intrinsically lack kinase activity (12, 13). JAK kinases, upon stimulation with factors such as erythropoietin, granulocyte-macrophage colony stimulating factor, IL-3, IL-5, thrombopoietin, and growth hormone, phosphorylate signal transducers and activators of transcription (STAT1-5) family proteins which are translocated to the nucleus and activate various downstream target genes involved in cytokine and growth factor response. JAK kinases play a role in inflammatory conditions, particularly those driven by cytokines including atopic dermatitis.

There is a need in the art for methods of treatment using compounds that are dual inhibitors of Syk/JAK for treating inflammatory disorders, such as atopic dermatitis.

SUMMARY

In one embodiment, the present disclosure relates to formulations, methods, kits, and dosage forms for treating conditions related to the inhibition of Syk/JAK, such as such as inflammatory disorders or cancers, characterized by the presence of solid tumors, particularly melanoma, colon cancer, non-small cell lung cancer, bladder cancer and breast cancer and/or the following cancers: prostate, head, neck, eye, mouth, throat, esophagus, bronchus, larynx, pharynx, chest, bone, rectum, stomach, uterus, cervix, ovaries, vagina, testicles, skin, thyroid, blood, lymph nodes, kidney, liver, intestines, pancreas, brain, central nervous system, adrenal gland, skin or a leukemia and/or lymphoma.

In one embodiment, the present disclosure relates to formulations, methods, kits, and dosage forms for treating conditions related to the inhibition of Syk/JAK, such as inflammatory disorders including atopic dermatitis.

In an embodiment, the pharmaceutical formulations described herein comprise granules, wherein the granules comprise a micronized active ingredient, one or more granulation binders, one or more fillers, one or more disintegrants and one or more antioxidants. The formulations may further comprise extragranular components. The active ingredient can be in the amount of about 20 mg to about 80 mg. The formulations described herein can be administered to a subject once daily for a short-term or long-term.

The active ingredient may comprise a compound of Formula (I) shown below, or a pharmaceutically acceptable salt or prodrug thereof,

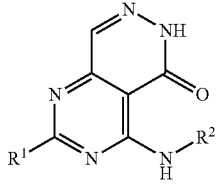

Formula (I)

wherein $R^1$ is a 6-membered ring of Formula (II):

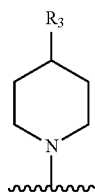

(II)

wherein $R^3$ is H, OH, C(O)OH, $C_1$ to $C_6$ alkyl or ($C_1$ to $C_6$) alkyl CN; and wherein $R^2$ is a benzene ring of Formula (III):

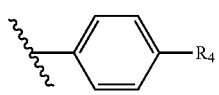

(III)

wherein $R_4$ is a 6-membered ring of Formula (IV):

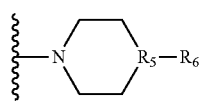

(IV)

wherein $R_5$ is N or CH and $R_6$ is a hydroxyl group, methyl group, or ethyl group, and wherein the formulation has a total API degradation impurity level not above about 0.6% of the total active ingredient amount after storage at 1 week at 40° C./75% RH in an open container.

In another embodiment, the present disclosure provides a dosage form comprising a pharmaceutical formulation comprising an active ingredient of formula (I) in a compressed tablet wherein the active ingredient in the pharmaceutical formulation retains stability after storage for a predetermined time and under predetermined conditions, including in an open container. In some embodiments, "storage in an open container" means that the container was opened once or twice a day for a given period of time, for example up to four weeks, but was otherwise left closed. In one embodiment, the formulation can be used to treat atopic dermatitis. In one embodiment, the active ingredient can be in an amount of about 20 mg to about 80 mg.

In another embodiment, the present disclosure provides a method of manufacturing or stabilizing a pharmaceutical formulation. The formulation can be useful for the treatment of atopic dermatitis. The method can comprise the steps of mixing intragranular ingredients comprising an active ingredient; one or more fillers; one or more disintegrants; and one or more antioxidants; granulating the mixed intragranular ingredients while adding a solution of 10% w/w of one or more granulation binders in 99% v/v isopropyl alcohol until granules are formed; and drying and milling the granules to make micronized granules; wherein the active ingredient comprises a compound of Formula (I) or a pharmaceutically acceptable salt or prodrug thereof and wherein the pharmaceutical formulation may further comprise extragranular components. In said embodiment, the active ingredient in the formulation retains stability and efficacy for a predetermined time and under predetermined conditions, including conditions wherein the container may be opened once or more than once. In one embodiment, the formulation can comprise an active ingredient in an amount of about 20 mg to about 80 mg.

In another embodiment, the present disclosure provides a kit comprising one or more dosage forms and instructions for administering the dosage forms to a subject, wherein the dosage forms comprise a pharmaceutical formulation comprising an active ingredient in substantially compressed tablet form optionally combined with extragranular components, wherein the active ingredient comprises a compound of the formula (I), wherein the active ingredient in the pharmaceutical formulation retains stability for a predetermined time and under predetermined conditions.

In another embodiment, the present disclosure provides a method of treating a condition characterized by dysregulation (e.g., abnormality or impairment) of Syk/JAK pathways in a subject. In one embodiment, the present disclosure provides a method of treating a condition characterized by dysregulation (e.g., abnormality or impairment) of Syk/JAK2 pathways in a subject. In another embodiment, the present disclosure provides methods for treating atopic dermatitis. The methods can comprise administering to the subject a therapeutically effective amount of an active ingredient in one or more dosage forms, wherein the dosage forms comprise a pharmaceutical formulation comprising an active ingredient in granular form in a compressed tablet optionally comprising one or more extragranular components, wherein the active ingredient comprises a compound of formula (I), wherein the active ingredient retains stability after storage of the pharmaceutical formulation for a predetermined time and under predetermined conditions. The dosage forms can comprise an active ingredient in the amount of about 20 mg to about 80 mg and can be administered to a subject once daily for a short-term period or a long-term period.

In another embodiment, the present disclosure provides a pharmaceutical formulation. The formulation can be useful for treating atopic dermatitis. The formulation can comprise an active ingredient in granular form in a compressed tablet optionally comprising one or more extragranular components, wherein the active ingredient comprises active ingredients of the formulations described herein wherein the active ingredient comprises 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile (sometimes referred to herein as "Compound 1"), or wherein the active ingredient comprises 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile. The active ingredient can be in the amount of about 20 mg to about 80 mg.

BRIEF DESCRIPTION OF FIGURES

FIG. 3 provides the 5-D Pruritus Scale.

FIG. 4 provides the Eczema Area and Severity Index (EASI) assessment tool.

FIG. 8A is a graph of the % CFB (percentage change from baseline) for EASI (decrease) for the placebo and Compound 1 in the doses of 20 mg, 40 mg and 80 mg, as demonstrated in Example 3.

FIG. 8B is a graph of the % CFB for IGA 0-1 (Investigator's Global Assessment) for the placebo and Compound 1 in the doses of 20 mg, 40 mg and 80 mg, as demonstrated in Example 3.

FIG. 8C is a graph of the % CFB for BSA (body surface area) (decrease) for the placebo and Compound 1 in the doses of 20 mg, 40 mg and 80 mg, as demonstrated in Example 3.

FIG. 11 is a chart showing Compound 1's inhibition of JAK/STAT pathway in T cells stimulated with various cytokines, as demonstrated in Example 3.

FIGS. 16A-16G provide clinical activity, safety and tolerability data for formulations of the present disclosure.

DETAILED DESCRIPTION

Figure 1:
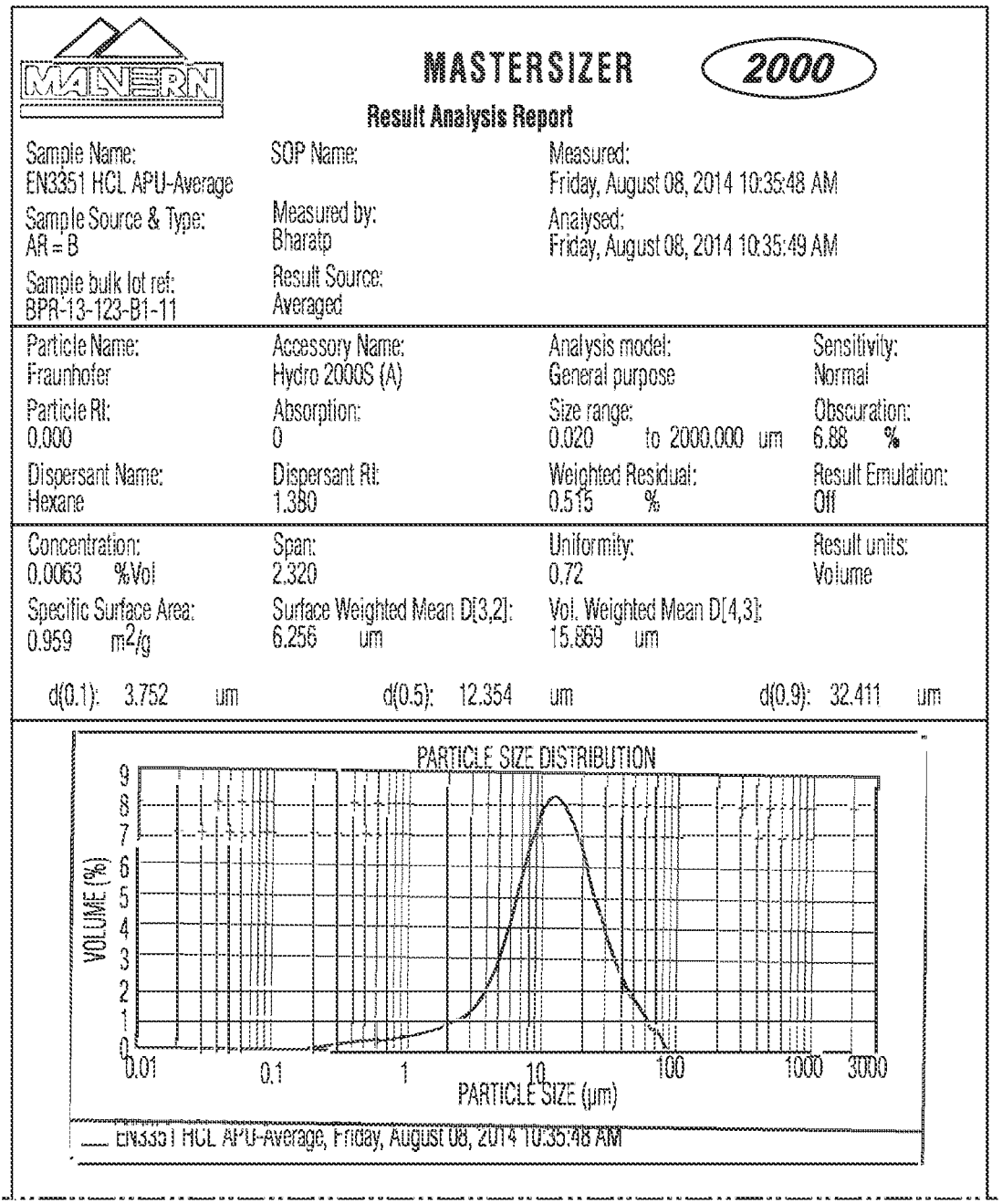
FIG. 1 provides a particle size distribution results analysis report for the active ingredient prior to micronization.

The following detailed description is exemplary and explanatory and is intended to provide further explanation of the present disclosure described herein. Other advantages, and novel features will be readily apparent to one of ordinary skill in the art from the following detailed description of the present disclosure.

The present disclosure provides one or more pharmaceutical formulations comprising an active ingredient in granular form compressed into a solid dosage form such as a tablet, methods of manufacturing such formulations, kits, methods of treating, and dosage forms wherein the active ingredient is configured to regulate the Syk/JAK pathway so that such formulations are capable of treating conditions associated with dysregulation in these pathways, including but not limited to, cancers and inflammatory disorders, for example atopic dermatitis.

The present disclosure comprises novel formulations comprising pyrimido-pyridazinone compounds. The formulations described herein are useful in treating cancer and inflammatory disorders in patients, for example atopic dermatitis, by administering one or more of the formulations to patients in need thereof. The formulations described herein are particularly desirable because of their unexpected superior stability profiles over a predetermined amount of time and because of their efficacy.

In an embodiment, the pharmaceutical formulations described herein comprise micronized granules, wherein the granules comprise an active ingredient, one or more granulation binders, one or more fillers, one or more disintegrants and one or more antioxidants. The formulations may further comprise extragranular components.

The active ingredient may comprise a compound of Formula (I) shown below, or a pharmaceutically acceptable salt or prodrug thereof,

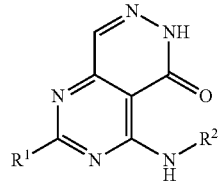

Formula (I)

wherein R¹ is a 6-membered ring of Formula (II):

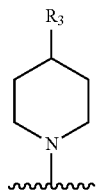

(II)

wherein R³ is H, OH, C(O)OH, $C_1$ to $C_6$ alkyl or ($C_1$ to $C_6$) alkyl CN; and
wherein R² is a benzene ring of Formula (III):

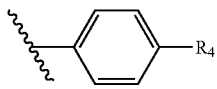

(III)

wherein R₄ is a 6-membered ring of Formula (IV):

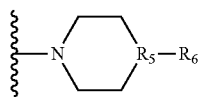

(IV)

wherein $R_5$ is N or CH and $R_6$ is a hydroxyl group, methyl group, or ethyl group, and wherein the formulation has a total API degradation impurity level not above about 0.6% of the total active ingredient amount after storage at 1 week at 40° C./75% RH in an open container.

Compounds of Formula (I) possess one or more chiral centers, and it is specifically contemplated that each separate enantiomer of compounds comprising an active ingredient of the disclosure, as well as mixtures of the enantiomers, can be used in the present formulations and methods. As disclosed herein, all chiral, enantiomeric and racemic forms of a chemical structure are intended, unless the specific stereochemistry is indicated. It is well known in the art how to prepare optically active forms of the compounds comprising active ingredients of the present formulations and methods, such as by resolution of racemic forms or by synthesis from optically active starting materials.

Active ingredients of the present disclosure can be prepared, for example, according to the methods disclosed in US Pat. Nos. U.S. Pat. Nos. 8,729,079 and 9,382,277, the entire disclosures of which are herein incorporated by reference. In some embodiments of the disclosure, an active ingredient comprising the pharmaceutical formulation of the disclosure can be present in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9% or 100% w/w.

The active ingredient for use in the present formulations and methods comprises compounds which regulate the Syk/JAK pathway. The regulatory activity of the active ingredients of the disclosure makes these compounds useful for manufacturing pharmaceutical formulations, which can be used for treating conditions such as inflammatory disorders, including atopic dermatitis, or cancers characterized by the presence of solid tumors, particularly melanoma, colon cancer, non-small cell lung cancer, bladder cancer and breast cancer.

In certain embodiments, the active ingredient is 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile. In other embodiments, the active ingredient is 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile.

The present disclosure thus provides for stable or stabilized pharmaceutical formulations comprising an active ingredient of the disclosure as described herein, for example stable or stabilized formulations comprising one or more compounds of formula (I), or enantiomers, prodrugs, pharmaceutically acceptable salts or free bases thereof. The stability of a formulation according to the present disclosure can be determined, for example, by measuring the physical state of the active ingredient. In one embodiment, the active ingredient retains stability and efficacy after storage for predetermined times and under predetermined conditions.

As used herein, the term "substantially granular" means that most of the active ingredient in the pharmaceutical compositions as described herein, is in the form of granules, preferably micronized granules, wherein such granules are compressed into a tablet. In certain embodiments, substantially granular means that the granules have a particle size of less than about 20 microns.

As discussed above, the active ingredient of the present disclosure is maintained in substantially granular form by combining the active ingredients with one or more stabilizing components. Suitable stabilizing components for use according to the present disclosure include one or more granulation binders; one or more fillers; one or more disintegrants; and one or more antioxidants, as further described herein.

The method by which the active ingredient and stabilizing component is formulated can also affect stability. For example, mixing intragranular ingredients comprising the active ingredient with one or more fillers; one or more disintegrants; and one or more antioxidants; granulating the mixed intragranular ingredients while adding a solution of 10% w/w of one or more granulation binders in 99% v/v isopropyl alcohol until granules are formed; and then drying and milling the granules to make micronized granules results in the formation of granules suitable for incorporating into a compressed tablet and for maintaining stability of a prolonged period.

In some embodiments, the formulations of the disclosure are stable when subject to predetermined conditions for predetermined times. For example, pharmaceutical formulations of the disclosure can be stored at various predetermined temperatures and relative humidities for defined or predetermined time periods, for example in an open or closed container. In some embodiments, formulations of the disclosure are stable upon storage at about 5, 25, 30, 37, 40 or 45 degrees Celsius and about 0%, 5%, 10%, 15%, 20%, 25%, 30%, 35%, 40%, 45%, 50%, 55%, 60%, 65%, 70%, 75%, 80%, 85%, 90%, 95% or 100% relative humidity for a period of at least about 0.5, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 48, 50, 51, 52, 53, 55 or 60 hours 1 week, 2 weeks, 3 weeks or 4 week; 1 month, 2 months, 3 months, 4 months, 5 months or 6 months.

In certain embodiments, formulations of the disclosure are stable upon storage in an open or closed container at: about 30 degrees Celsius and about 90 percent relative humidity for a period of at least about 20 hours; about 40 degrees Celsius and about 60 percent relative humidity for a period of at least about one week, two weeks or three weeks; about 40 degrees Celsius and about 75 percent relative humidity for a period of at least about one week, two weeks or three weeks; about 25 degrees Celsius and about 60 percent relative humidity for a period of at least about one month; about 40 degrees Celsius and about 75 percent relative humidity for a period of at least one month; about 25 degrees Celsius and about 75 percent relative humidity for a period of at least about 3 months; or 5 degrees Celsius at any relative humidity for a period of at least about three months. In some embodiments, "storage in an open container" means that the container was opened twice a day for a given period of time, for example up to four weeks, but was otherwise left closed.

In another embodiment, the formulation comprises the active ingredient 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile or the active ingredient 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile and is stable upon storage in an open or closed container at: about 30 degrees Celsius and about 90 percent relative humidity for a period of at least about 20 hours; about 40 degrees Celsius and about 60 percent relative humidity for a period of at least about one week, two weeks or three weeks; about 40 degrees Celsius and about 75 percent relative humidity for a period of at least about one week, two weeks or three weeks; about 25 degrees Celsius and about 60 percent relative humidity for a period of at least about one month; about 40 degrees Celsius and about 75 percent relative humidity for a period of at least one month; about 25 degrees Celsius and about 75 percent relative humidity for a period of at least about 3 months; or 5 degrees Celsius at any relative humidity for a period of at least about three months.

The pharmaceutical formulations of the disclosure can also be tested for other physical characteristics, for example by evaluating the amount of active ingredient and/or impurity levels of the formulations at the end of a predetermined time period after they have been subjected to predetermined conditions, for example, temperature and relative humidity in open and closed containers. Suitable methods for measuring the impurity profile of the present formulations are known in the art. Exemplary methods for measuring the impurity profile of the present formulations may involve any suitable chromatographic separation methods, such as high-pressure liquid chromatography (HPLC) comprising the use of separation column and gradient elution as are known to those of ordinary skill in the art. An exemplary HPLC method for evaluating the amount of active ingredient and/or impurity levels of the pharmaceutical formulations of the present disclosure is described in Example 1 below. In addition, other methods may be utilized instead of or in addition to HPLC separation methods, including capillary electrophoresis, electron paramagnetic resonance, gas-liquid chromatography, gravimetric analysis, solid-phase extraction methods, liquid-liquid extraction method, ultraviolet spectrometry, infrared spectroscopy, supercritical fluid extraction column chromatography, mass spectrometry, nuclear magnetic resonance (NMR) spectroscopy, and RAMAN spectroscopy.

In some embodiments, the impurity test comprises subjecting the formulation to storage conditions at 40 degrees Celsius at 75% relative humidity in open and closed containers. In another embodiment, the impurity test comprises subjecting the formulation to storage conditions under accelerated stress conditions at 60 degrees Celsius in closed containers. In another embodiment, the formulations may be evaluated for impurity levels following storage at 40 degrees Celsius at 75% relative humidity in open containers for one week.

The pharmaceutical formulations of the disclosure can also be tested for physical characteristics, such as Vitamin E content, by use of any suitable analytical method, for example an HPLC method comprising isocratic elution with water and acetonitrile as the mobile phase and UV detection as described in Example 1 below.

Although exemplary amounts or ranges for the active ingredient and other components are given, pharmaceutical formulations of the disclosure can comprise any amount of these components suitable for the purposes of obtaining the desirable pharmacologic and stability properties as described herein. In addition to the active ingredient, pharmaceutical compositions of the disclosure can also comprise other pharmaceutically acceptable excipients, for example adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, thickening agents, or viscosity regulators. Suitable excipients for use in pharmaceutical compositions of the disclosure are described, for example, in the "Handbook of Pharmaceutical Excipients", 5th Edition, Eds.: Rowe, Sheskey, and Owen, APhA Publications (Washington, D.C.), Dec. 14, 2005, the disclosure of which is incorporated herein by reference.

In certain embodiments, pharmaceutical compositions of the disclosure can be compacted into a unit dose form, e.g., tablet or caplet, or added to unit dose form, e.g., a compressed tablet. In a further embodiment, pharmaceutical compositions of the disclosure can be formulated for administration as micronized granules or as a suspension of micronized granules. A pharmaceutical formulation of the disclosure which comprises micronized granules or a suspension thereof can, for example, be sprinkled on or mixed with a semi-solid carrier such as apple sauce or another food item for administration to a subject. The which comprises micronized granules or a suspension thereof can also, for example, be added to a liquid carrier suitable for administration to subjects, such as a solution of about 2% w/V hydroxypropyl cellulose and about 0.1% w/V polysorbate 80 in water or about 0.2% hydroxypropylcellulose, and 0.1% Tween 80 in water, to form a suspension.

In one embodiment, the dosage form of the disclosure comprises a compressed tablet, for example at about 25, 50, 75, 80 or 100 mg strengths. In another embodiment, the dosage form of the disclosure comprises a capsule, for example at about 25, 50, 75, 80 or 100 mg strengths. In a further embodiment, the dosage form of the disclosure is a tablet comprising micronized granules of the active ingredient, for example at about 25, 50, 75, 80 or 100 mg strengths. In another embodiment, the dosage form of the disclosure is a capsule comprising micronized granules for example at about 25, 50, 75, 80 or 100 mg strengths. In one embodiment, the dosage form of the disclosure is a capsule comprising micronized granules for example at about 75 mg strength.

Suitable techniques for formulating pharmaceutical compositions of the disclosure into tablets are well-known in the art, and can comprise mixing the active ingredient and stabilizing components with one or more pharmaceutically acceptable tableting excipients and compressing the mixture into a tablet, for example with a tableting press. The amount and nature of the tableting excipients used can be readily chosen based on the desired characteristics of the tablet, such as size, hardness, friability and the like. Tablets comprising pharmaceutical compositions of the disclosure can also be coated, for example with film coatings like Opadry White@, or with enteric coatings designed to prevent dissolution of the tablets until the transit the stomach and/or upper intestine. Suitable tablet coatings and methods for applying them are well-known in the art.

Suitable techniques for formulating pharmaceutical compositions of the disclosure into capsules are also well-known in the art, and can comprise mixing the active ingredient and stabilizing components with one or more pharmaceutically acceptable capsule excipients and filling the mixture into a capsule. In one embodiment, a pharmaceutical formulation of the disclosure (with or without additional excipients) can be filled into a capsule, such as a hard gelatin capsule. The hard gelatin capsule can be of any appropriate size, for example size '0', '0EL', '3', '4' and the like. For example, in one embodiment a capsule of the disclosure having a dosage strength of 25 mg of the active ingredient can be filled into a hard gelatin capsule of size 4, where the target capsule fill weight can comprise 100 mg. In another embodiment, a capsule of the disclosure having a dosage strength of 100 mg of the active ingredient can be filled into a hard gelatin capsule of size 0el, where the target capsule fill weight can comprise 400 mg.

Also provided herein are kits comprising at least one dosage form of the disclosure, for example a tablet or capsule, and instructions for administering the at least one dosage form to a subject. The kit can also comprise packaging or a container housing the at least one dosage form of the disclosure, and can also comprise instructions on storage, administration, dosing or the like and/or an insert regarding the active ingredient. The kit can also comprise instructions for monitoring circulating levels of the active ingredient (or metabolites thereof) once administered, and optionally materials for performing such assays including, e.g., reagents, well plates, containers, markers or labels, and the like. Other suitable components to include in kits of the disclosure will be readily apparent to one of skill in the art, taking into consideration the desired indication, dosing regimen, storage conditions and route of administration.

The pharmaceutical compositions of the disclosure can formulated for administration as a single dose or as multiple doses for continuous or periodic discontinuous administration. For continuous administration, a kit can include the pharmaceutical compositions of the disclosure in individual unit dosage forms (e.g., tablet or capsule), and optionally instructions for administering the individual unit dosage forms, for example, more than once daily, twice a day (BID), four times a day (QID), daily, weekly, or monthly, for a predetermined length of time or as prescribed. When the pharmaceutical compositions of the disclosure are to be delivered periodically in a discontinuous fashion, a kit can include placebos during periods when the individual unit dosage forms are not delivered. In some embodiments, formulations of the present disclosure can be administered at a dose of about 10 mg BID, about 20 mg BID, about 30 mg BID, about 40 mg BID, about 50 mg BID, about 75 mg BID, about 100 mg BID, about 80 mg QID, or about 120 mg QID. In one embodiment, formulations of the present disclosure can be administered at a dose of about 75 mg BID.

Suitable packages or containers are known in the art for holding and dispensing pharmaceutical agents for periodic oral use. In one embodiment, the package comprises indicators for each administration period. In another embodiment, the package comprises a labeled blister package, dial dispenser package, or bottle. The kits of the disclosure can also comprise a means for containing any type of packaging that houses the unit dosage forms, for example bottles or vials, which can (for example) be held in close confinement for commercial sale such as, e.g., injection or blow-molded plastic containers into which the bottles or vials are retained.

The pharmaceutical compositions, methods of treatment, dosage forms and kits of the disclosure are useful in treating conditions which are associated with dysregulation (e.g., abnormality or impairment) of the Syk/JAK pathway. In one embodiment, the conditions are associated with dysregulation of the Syk/JAK2 pathway. In one embodiment, a condition associated with dysregulation of the Syk/JAK pathway comprises acute or chronic inflammatory disorders, such as atopic dermatitis. In one embodiment, a condition associated with dysregulation of the Syk/JAK pathway comprises a disease that is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, for example cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma. In one embodiment, the disease characterized by abnormal cellular proliferation is cancer of the prostate. In another embodiment, the abnormal cellular proliferation is associated with at least one solid tumor.

In one embodiment, the pharmaceutical compositions, methods of treatment, dosage forms and kits of the disclosure are useful in treating conditions including (without limitation) peripheral T-cell lymphoma (PTCL), chronic lymphocytic leukemia (CLL), myelofibrosis (MF), for example primary myelofibrosis (PMF), essential thrombocytopenia (ET), and polycythemia vera (PV), mature B-cell neoplasms, for example diffuse large B-cell lymphoma (DLBCL), both germinal B-cell (GCB) as activated B-cell (ABC) subtypes, mantle cell lymphoma, high grade B-cell lymphoma (HGBL), anaplastic large cell lymphoma, marginal zone lymphoma, hairy cell leukemia, Waldenstrom macroglobulinemia, Monoclonal gammopathy of undetermined significance (MGUS), plasma cell myeloma, Burkitt lymphoma, Mature T and NK neoplasms, Hodgkin lymphoma, posttransplant lymphoproliferative disorders (PTLD), histiocytic and dendritic cell neoplasms, myeloid neoplasms, for example PV, ET, primary myelofibrosis, chronic neutrophilic leukemia, chronic myeloid leukemia, atypical chronic myeloid leukemia, juvenile myelomonocytic leukemia, and acute myeloid leukemia, precursor lymphoid neoplasm, for example, B-cell acute lymphoblastic leukemia (B-ALL), Down Syndrome ALL, T-cell ALL (T-ALL), Mature lymphoid neoplasms, for example, T-cell prolymphocytic leukemia, adult T-cell leukemia/lymphoma (ATLL), Natural Killer/T-cell lymphoma (NK/TCL), NK/T—Large Granular Lymphocytic Leukemia (NK/T-LGL), primary mediastinal large B-cell lymphoma/Hodgkin lymphoma (PBMCL/HL) and follicular lymphoma (FL), primary cutaneous lymphoma (PCL), for example, mycosis fungoides/Sezary syndrome, and/or peripheral T-cell lymphoma (PTCL). Further conditions include (without limitation) acute and chronic graft-versus host Disease (aGVHD and cGVHD) and treatment of immune mediated complications of checkpoint inhibitors or other immune-oncology therapies. A list of JAK or SYK driven hematologic malignancies is found in the 2016 revision of the World Health Organization (WHO) classification of lymphoid neoplasms; Blood 2016 127:2375-2390, which is incorporated by reference herein. A list of hemotologic malignancies with known JAK mutations is found at Haematologica. 2015 October; 100(10): 1240-1253, which is incorporated by reference herein.

In another embodiment, a condition associated with dysregulation of the Syk/JAK pathway comprises acute or chronic inflammatory disorders, such as neutrophil-associated inflammation, inflammatory arthritis, inflammation in peritonitis, inflammation after myocardial infarction or bleomycin-induced pulmonary fibrosis. Models for testing the ability of compounds to reduce inflammation in inflammatory arthritis are known, e.g., as described by Camps et al, Nature Med., 2005, 11, 936-943, which also describes models useful in assessing the ability of compounds to reduce inflammation in peritonitis; models for testing the ability of compounds to reduce inflammation and/or improve healing after myocardial infarction are described by Siragusa et al, Circ. Res. (2010), 106, 757-768; and a model for testing the ability of compounds to prevent bleomycin-induced pulmonary fibrosis is described by Wei et al, Biochem Biophys Res Comm. 2010, 397: 311-317 and Brent et al, Toxicology, 2000, 147: 1-13, the entire disclosures of which are incorporated herein by reference.

In one embodiment, the present disclosure provides formulations, methods, kits, and dosage forms for broadly treating all autoimmune diseases, including, for example (without limitation), atopic dermatitis, alopecia areata, hand and foot eczema, hidradenitis suppurativa, pemphigus vulgaris, psoriasis, cutaneous lupus, vitiligo, inflammatory bowel disease (UC, CD), rheumatoid arthritis, asthma, allergic rhinitis, systemic lupus erythematosus (SLE), psoriatic arthritis, and multiple sclerosis (including other autoimmune diseases).

The disclosure thus provides a method of treating a disease characterized by the dysregulation (e.g., abnormality or impairment) of the Syk/JAK pathway in a subject, comprising administering to the subject a therapeutically effective amount of an active ingredient in one or more dosage forms, wherein the dosage forms comprise a pharmaceutical formulation comprising an active ingredient, wherein the active ingredient in the form of micronized granules is formed into a compressed tablet, wherein the active ingredient comprises a compound of the formula (I), and wherein the active ingredient retains stability after storage of the pharmaceutical formulation for a predetermined time and under predetermined conditions.

As described herein, a therapeutically effective amount of an active ingredient of the disclosure when used for the treatment of cancer is, for example, an amount which may reduce the number of cancer cells in fluids (e.g., blood, peripheral cells or lymphatic fluids), reduce tumor size, inhibit metastasis, inhibit tumor growth and/or ameliorate one or more of the symptoms of the cancer. For cancer therapy, efficacy can be measured for example, by assessing the time to disease progression and/or determining the response rate, or measuring inhibition of tumor growth or metastasis. In one embodiment, administration of the formulations described herein can achieve inhibition of tumor growth in an amount of 0% to 100%, preferably an amount of above about 50%.

As described herein, a therapeutically effective amount of an active ingredient of the disclosure when used for the treatment of an inflammatory disorder, such as atopic dermatitis, is an amount which may delay the onset of or reduce the severity or duration of an inflammatory response, or which mitigates one or more symptoms of an inflammatory response. For treatment of an inflammatory disorder, efficacy can be measured, for example, by a reduction in physiologic signs of inflammation (e.g., redness, swelling, heat, loss of function) or by measuring changes in the levels of cells (e.g., monocytes, macrophages and other mononuclear cells) or molecules (e.g., pro-inflammatory cytokines) associated with inflammation. In one embodiment, treatment of atopic dermatitis can be measured by evaluating a subject according to the Investigators Global Assessment (IGA) scale, the 5-D Pruritus Scale, the Pruritus Numeric Rating Scale or the Eczema Area and Severity Index (EASI) assessment tool, as described, for example, in FIGS. 3 and 4 and in Example 3 below.

The Syk/JAK pathways are known to be deregulated in various cancers due to specific mutations in different members of each pathway. For example aberrations in Syk/JAK pathways, such as those caused by the recently identified $JAK2^{V617F}$ mutation and translocations of the JAK2 gene, are underlying causes of leukemias and other myeloproliferative disorders. Such mutations are easily detected in tumor samples using methods known in the art Sarkar et al (Diagn Mol Pathol. (1995) 4(4):266-73), the entire disclosure of which is herein incorporated by reference.

Identifying a mammalian subject, e.g., a human patient, or a population of such subjects who will respond positively to treatment with pharmaceutical formulations of the disclosure prior to initiation of treatment (also termed herein "predetermining" or "selecting") can be accomplished by assaying a sample (for example a tumor biopsy or blood sample comprising white blood cells when the condition is cancer) from a patient to detect one or more of the Syk/JAK mutations discussed above. Upon detection of a Syk/JAK mutation, the subject may be treated with the pharmaceutical formulations of the present disclosure, for example by administering one or more pharmaceutical formulations of the present disclosure which comprise a therapeutically effective amount of an active ingredient as described herein.

A suitable sample may be obtained from the body of a subject and may include, e.g., tissue samples, cells, extracellular matter, or circulating cancer cells in blood or lymphatic fluid. Tissue samples may be from any organ, including disease states of such organs, such as the skin, the blood circulatory system, and any circulating tumor cells. Tissue samples such as tumor biopsies may be obtained using known procedures. Tissue specimens may also include xenograft tumor samples, e.g., those from animals used in drug dose or toxicology studies.

For example, a subject can be tested for the presence of a $JAK2^{V617F}$ mutation. As discussed above, these mutations can be detected using any suitable technique known in the art, including fluorescence in situ hybridization, PCR-based sequencing of relevant portions of a given gene, restriction fragment length polymorphism analysis, or by monitoring expression levels of a given gene product (e.g., protein or RNA). In one embodiment, a method is provided for treating a condition treatable by inhibiting the Syk/JAK pathway, comprising selecting a subject who has a $JAK2^{V617F}$ mutation; and administering a therapeutically effective amount of a pharmaceutical formulation of the disclosure. In one embodiment, a method is provided for treating patients whose cancers are characterized by the presence of the JAK2$^{v617F}$ mutation and translocation of the JAK2 gene comprising the steps of identifying patients having such mutation(s) and administering a therapeutically effective amount of the formulation disclosed herein.

In an embodiment, the present disclosure provides pharmaceutical formulations comprising granules, wherein the granules comprise: micronized active ingredient; one or more granulation binders; one or more fillers; one or more disintegrants; and one or more antioxidants, wherein the active ingredient is a compound of Formula (I) or a pharmaceutically acceptable salt or prodrug thereof, and wherein the formulation may further comprise extragranular components. In an embodiment, the active ingredient comprises 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile. In another embodiment, the active ingredient comprises 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile.

In an embodiment, the antioxidants of the formulations described herein may include vitamin E or butylated hydroxytoluene; the fillers may comprise lactose monohydrate; the distintegrants may comprise crospovidone or croscarmellose sodium and the granulation binders may comprise polyvinylpyrollidone or hydroxypropylcellulose. In certain embodiments, the granulation binders comprise hydroxypropylcellulose having a viscosity at 25° C. of 75-150 centipoise in a 5% w/w in aqueous solution. In certain embodiments, the granulation binders comprise polyvinylpyrollidone having a number average molecular weight of about 30,000. In an embodiment, the micronized granules of the presently described formulation have a particle size of less than about 20 microns. In an embodiment, the micronized granules have an isopropyl alcohol content of less than about 5000 ppm.

In certain embodiments, the formulations may comprise one or more extragranular components. The extragranular components may comprise one or more tableting fillers, one or more disintegrants, one or more lubricants, and optionally one or more surfactants. In certain embodiments, the tableting fillers may comprise microcrystalline cellulose, the disintegrants may comprise croscarmellose sodium, the surfactants may comprise sodium lauryl sulfate, and the lubricants may comprise magnesium stearate. In an embodiment, the micronized granules and extragranular components may be compressed into a tablet.

The formulations of the present disclosure may exist in any embodiment known to one skilled in the art. In an embodiment, the formulation may be present in the form of tablets, scored tablets, compressed tablets, coated tablets, capsules, caplets, pills, powder packets and modifications thereof. In an embodiment, the formulation described herein comprises compressed tablets.

In an embodiment the micronized granules of the present formulation have an isopropyl alcohol content of less than about 5000 ppm. The active ingredient in the embodiments described herein may be between about 5 to 50 mg, 5 mg, about 20 mg, or about 50 mg. Other aspects of the embodiments described herein may include a tablet hardness of approximately 5-12 kP, or 7 to 9 kP and a disintegration time of less than about 5 minutes in 0.1 N HCl, pH 6.8 and 50 mM phosphate buffer at 37° C. In certain embodiments the formulations may comprise a tablet having an aesthetic coating; the coating may be comprised of hydroxypropylcellulose, titanium dioxide, talc and polyethylene glycol.

In an embodiment, the formulation described herein comprises a compressed tablet having micronized granules and extragranular components, wherein: the tablet has a total weight of about 150 mg; the micronized granules comprise about 5 to 50 mg of an active ingredient, about 75 to 900 mg, or 118.6 to 736 mg of lactose monohydrate, about 1-20 mg, or 4.5 mg croscarmellose sodium, about 0.1-5 mg or 0.15 mg vitamin E, and about 1-10 mg, or 4.5 mg granulation binder; furthermore, the extragranular components may comprise about 5-20 mg, or 11.25 mg or microcrystalline cellulose, about 1-10 mg or 4.5 mg croscarmellose sodium, about 1-10 mg or 1.5 mg magnesium stearate, and about 1-10 mg or 6 mg of an enteric coating. The active ingredient in such an embodiment may comprise 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile.

In certain embodiments of such a compressed tablet, granulation binders maybe selected from the group consisting of polyvinylpyrollidone and hydroxypropylcellulose wherein hydroxypropylcellulose has a viscosity at 25° C. of 75-150 centipoise in a 5% w/w in aqueous solution. In certain embodiments, the micronized granules comprise about 75-150 mg, or 117.1 mg to about 72.1 mg of lactose monohydrate and the extragranular components further comprise about 1-10 mg or 1.5 mg sodium lauryl sulfate.

In certain embodiments, the micronized granules of a compressed tablet as described herein may comprise about 5 mg of an active ingredient and about 118.6 mg of lactose monohydrate, about 20 mg of an active ingredient and about 103.6 mg of lactose monohydrate, or about 50 mg of an active ingredient and about 73.6 mg of lactose monohydrate.

Further included herein are embodiments comprising methods of manufacturing the pharmaceutical formulation embodiments described above. Also included are methods of preparing compressed tablets and methods of stabilizing pharmaceutical formulations as well as the preparation of dosage forms comprising micronized granules and extragranular components compressed into a tablet. In an embodiment, the methods, protocols and procedures regarding the foregoing comprise the incorporation of an active ingredient together with antioxidants including vitamin E or butylated hydroxytoluene; fillers comprising lactose monohydrate; disintegrants comprising crospovidone or croscarmellose sodium and granulation binders comprising polyvinylpyrollidone or hydroxypropylcellulose. In certain embodiments, the granulation binders comprise hydroxypropylcellulose having a viscosity at 25° C. of 75-150 centipoise in a 5% w/w in aqueous solution. In certain embodiments, the granulation binders comprise polyvinylpyrollidone having a number average molecular weight of about 30,000. In an embodiment, the micronized granules of the presently described embodiments have a particle size of less than about 20 microns. In an embodiment, the micronized granules have an isopropyl alcohol content of less than about 5000 ppm.

In an embodiment, the formulations may further comprise one or more extragranular components. The extragranular components may comprise one or more tableting fillers, one or more disintegrants, one or more lubricants, and optionally one or more surfactants. In certain embodiments, the tableting fillers may comprise microcrystalline cellulose, the disintegrants may comprise croscarmellose sodium, the surfactants may comprise sodium lauryl sulfate, and the lubricants may comprise magnesium stearate. In an embodiment, the micronized granules and extragranular components may be compressed into a tablet.

In an embodiment, the active ingredient for the foregoing may comprise 2-(1-(4-((4-(4-hydroxypiperidin-1-yl)phenyl) amino)-5-oxo-5,6-dihydropyrimido[4,5-d]pyridazin-2-yl) piperidin-4-yl)acetonitrile. In another embodiment, the active ingredient may comprise 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile.

In the above embodiments, the methods of manufacturing and producing may comprise mixing intragranular ingredients comprising an active ingredient; one or more fillers; one or more disintegrants; and one or more antioxidants; granulating the mixed intragranular ingredients while adding a solution of 10% w/w of one or more granulation binders in 99% v/v isopropyl alcohol until granules are formed; drying and milling the granules to make micronized granules; wherein the active ingredient comprises a compound of Formula (I) or a pharmaceutically acceptable salt or prodrug thereof.

In a further embodiment, kits comprising one or more dosage forms and instructions for administering the dosage forms to a subject, wherein the dosage forms comprise granules and extragranular components compressed into a tablet, are also provided. In such embodiments, the formulation may comprise the active ingredients comprising 2-(1-(4-((4-(4-hydroxypiperidin-1-yl)phenyl)amino)-5-oxo-5,6-dihydropyrimido[4,5-d]pyridazin-2-yl)piperidin-4-yl) acetonitrile. In another embodiment, the active ingredient may comprise 2-(1-(4-((4-(4-(2-hydroxyethyl)piperazin-1-yl)phenyl)amino)-5-oxo-5,6-dihydropyrimido[4,5-d] pyridazin-2-yl)piperidin-4-yl)acetonitrile.

The above embodiments may be utilized in methods for treating cancer or atopic dermatitis or inflammation in a subject, comprising administering to the subject a therapeutically effective amount of an active ingredient in one or more dosage forms, wherein the dosage forms comprise micronized granules and extragranular components compressed into a tablet.

Active ingredients of the present disclosure can be prepared, for example, according to the methods disclosed in US Pat. Nos. U.S. Pat. Nos. 8,729,079 and 9,382,277, the entire disclosures of which are herein incorporated by reference. In some embodiments of the disclosure, an active ingredient comprising the pharmaceutical formulation of the disclosure can be present in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9% or 100% w/w.

The active ingredient for use in the present formulations and methods comprises compounds which regulate the Syk/JAK pathway. The regulatory activity of the active ingredients of the disclosure makes these compounds useful for manufacturing pharmaceutical formulations, which can be used for treating conditions such as inflammatory disorders, including atopic dermatitis, or cancers characterized by the presence of solid tumors, particularly melanoma, colon cancer, non-small cell lung cancer, bladder cancer, and breast cancer.

The therapeutically effective amount of a pharmaceutical formulation of the disclosure provided to a subject will vary depending upon the purpose of the administration, the state of the patient, level of disease penetration and the like. As used herein, "subject" includes any human or non-human animal in need of treatment with the pharmaceutical formulations of the disclosure. In one embodiment, a subject is any human in need of treatment with the formulations of the disclosure (sometimes referred to herein as a "patient"). A therapeutically effective amount of the active ingredient in the pharmaceutical formulations of the disclosure can be determined by an ordinarily skilled physician or medical professional, taking into account certain variables, including the specific condition and the size, age, weight, gender, disease penetration, previous treatment and response pattern of the patient.

In one embodiment, the pharmaceutical formulation is administered orally, for example in capsule or tablet form. For example, the present formulations can be provided as a unit dose, for example as a compressed tablet, comprising a therapeutically effective amount. In one embodiment, a unit dose comprising the pharmaceutical formulation of the disclosure can be administered once daily or multiple times daily, for example, 1 to 6 times in a 12 or 24 hour period. If multiple unit doses are administered in a given time period, they can be administered at substantially even time intervals. For example, if two unit doses are administered in a 12 hour period, they can be given to the patient 6 hours apart. Multiple unit doses are administered in a given time period can also be administered at substantially uneven time intervals. In one embodiment, a unit dose comprises a dosage form of the disclosure in the form of a tablet or capsule for oral administration.

In some embodiments, the active ingredient in the pharmaceutical formulations of the disclosure can comprise an amount of about 0.5 to 100 percent by weight, for example about 0.5, 1, 1.5, 2, 2.5, 5, 10, 15, 20, 25, 30, 35, 40, 45, 50, 55, 60, 65, 70, 75, 80, 85, 90, 95, 96, 97, 98, 99 or 100 percent by weight. In another embodiment, the active ingredient comprises about 3.5 percent or about 14 percent of the pharmaceutical formulation by weight.

In some embodiments, formulations of the disclosure comprise an active ingredient of the disclosure, formed into oral dosage forms such as tablets, capsules, powders, suspensions, and the like. In such dosage forms of the disclosure, the amount of active ingredient comprising the dosage form can be any suitable amount, for example about 0.5, 1, 1.5, 2, 2, 5, 5, 10, 15, 20, 25, 30, 35, 40, 45, 50, 55, 60, 65, 70, 75, 80, 85, 90, 95, 96, 97, 98, 99 or 100 mg per unit dosage form. In certain embodiments, dosage forms of the disclosure comprise about 20 to about 80 mg of the active ingredient per dosage form.

In certain embodiments, formulations of the disclosure comprise an active ingredient of the disclosure, formed into dosage forms such as tablets, capsules, sachets, powders, suspensions, suppositories and the like. In such dosage forms of the disclosure, the amount of active ingredient comprising the dosage form can be any suitable amount, for example about 0.5, 1, 1.5, 2, 2, 5, 5, 10, 15, 20, 25, 30, 35, 40, 45, 50, 55, 60, 65, 70, 75, 80, 85, 90, 95, 96, 97, 98, 99 or 100 mg per unit dosage form. In certain embodiments, dosage forms of the disclosure comprise about 25, 50, 75, 80 or 100 mg of the active ingredient per dosage form. In one embodiment, dosage forms of the disclosure comprise about 75 mg of the active ingredient per dosage form.

A suitable daily (i.e. 24 hour time period) dose according to methods of the disclosure, whether given all at once or in multiple administrations, can depend on the specific method of treatment and condition treated. In one embodiment, a suitable daily dose, whether given all at once or in multiple administrations, is between about 10 to 120 mg for oral application, for example about 20 mg to 80 mg, 25 to 75 mg, 30 mg to 70 mg, 35 mg to 65 mg, or 40 mg to 60 mg. In one embodiment, a suitable daily dose is between about 40 mg to about 80 mg. In other embodiments, a suitable daily dose is about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg or 120 mg. In one embodiment, a suitable daily dose is about 20 mg. In another embodiment, a suitable daily dose is about 40 mg. In another embodiment, a suitable daily dose is about 80 mg.

In another embodiment, a suitable daily (i.e. 24 hour time period) dose according to methods of the disclosure, whether given all at once or in multiple administrations, can depend on the specific method of treatment and condition treated. In one embodiment, a suitable daily dose, whether given all at once or in multiple administrations, is between about 10 to 1000 mg for oral application, for example about 20 to 500 mg, 50 mg to 250 mg or 75 mg to 100 mg. In other embodiments, a suitable daily dose is about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 200 mg, 250 mg, 300 mg, 400 mg, 500 mg, 600 mg, 700 mg, 800 mg, 900 mg or 1000 mg.

In another embodiment, a suitable daily dose, whether given all at once or in multiple administrations, is about 0.1 mg/kg to about 100 mg/kg, about 0.5 mg/kg to about 75 mg/kg, about 0.1 mg/kg, 1 mg/kg, 10 mg/kg, 20 mg/kg, 30 mg/kg, 40 mg/kg, 50 µg/kg, 75 µg/kg or 100 µg/kg.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. Alternatively, equivalent doses may be administered over uneven intervals in accordance with the recommended treatment of a health-care practitioner. The number and frequency of dosages corresponding to a completed course of therapy will be determined according to the judgment of a health-care practitioner. The therapeutically effective amounts described herein refer to total amounts administered for a given time period; that is, if more than one active ingredient is administered, the therapeutically effective amounts correspond to the total amount administered.

In one embodiment, the pharmaceutical formulation is administered orally once a day (QD). The administration can be short-term or long-term. For example, short term administration can comprise administration of the pharmaceutical formulation once a day for about 1 week, 2 weeks, 3 weeks or 4 weeks, or any other longer or shorter term. For example, long term administration can comprise administration of the pharmaceutical formulation once a day for at least 1 week, 2 weeks, 3 weeks, 4 weeks, 30 days, 1 month, 2 months, 3 months, 6 months, 1 year, 2 years, or 5 years, or any other longer or shorter term.

The following examples are given to illustrate exemplary embodiments of the present disclosure. It should be understood, however, that the present disclosure is not to be limited to the specific conditions or details described in these examples.

EXAMPLES

Example 1

Preformulation, Formulation and Analytical Data

Analytical studies for 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile are provided below in Tables 1-3: Table 1 provides the results of an HCl pH dependent solubility profile study, Table 2 provides the results of an HCl solubility profile in organic solvents, and Table 3 provides the results of an HCl stress study.

TABLE 1

|  | 0.1N HCl | pH 4.5 Acetate Buffer | pH 5.5 Acetate Buffer | pH 6.8 Phosphate Buffer | pH 7.5 Phosphate Buffer | Water |
|---|---|---|---|---|---|---|
| Initial pH | N/A | 4.50 | 5.52 | 6.80 | 7.55 | N/A |
| End pH | 1.23 | 4.56 | 5.12 | 6.86 | 6.96 | 2.62 |
| Solubility µg/mL | 10810 | 2.9 | 1.0 | 2.7 | 0.7 | 941 |

TABLE 2

|  | MeOH | EtOH | IPA |
|---|---|---|---|
| Solubility µg/mL | 4437 | 4996 | 462 |

TABLE 3

|  | 1N HCl rt, 24 hr | 1N NaOH rt, 24 hr | 3% H2O2 rt, 30 hr | 80° C. 24 hr | UV 23 hr |
|---|---|---|---|---|---|
| % API based on Peak Area % | 100.00% | 99.54% | 83.00% | 99.93% | 99.80% |

Studies were conducted to evaluate excipient compatibility, stability and disintegration comprising the use of Ac-Di-Sol and Polyplasdone XL-10; PVP K-30 and Klucel LF and SLS. Water was avoided as a granulating solved and IPA was used. The coating comprised Opadry (IPA/water, 50/50) and tables were prepared in 5/20/50 mg strength, 150 mg weight (DT: <5 min in 0.1 N HCl, pH 6.8, 50 mM P04 buffer). Details concerning ingredients and relative weights for prototype formulation A and formulation B are provided below in Table 4.

TABLE 4

| Ingredients | Formulation A mg/tab | Batch (g) | Formulation B mg/tab | Batch (g) |
|---|---|---|---|---|
| Intragranular | | | | |
| API | 5/20/50 | 1.50 | 5 | 1.50 |
| Lactose Monohydrate | 117.25/lower | 35.18 | 118.75 | 35.63 |
| Primellose | 4.5 | 1.35 | 0 | 0.00 |
| Polyplasdone XL-10 | 0 | 0.00 | 4.5 | 1.35 |
| Klucel LF/PVP K-30 | 4.5 | 1.35 | 4.5 | 1.35 |

TABLE 4-continued

| Ingredients | Formulation A mg/tab | Batch (g) | Formulation B mg/tab | Batch (g) |
|---|---|---|---|---|
| Extragranular | | | | |
| Vivapur 101 | 11.25 | 3.38 | 11.25 | 3.38 |
| Primellose | 4.5 | 1.35 | 0 | 0.00 |
| Polyplasdone XL-10 | 0 | 0.00 | 4.5 | 1.35 |
| Magnesium Stearate | 1.5 | 0.45 | 1.5 | 0.45 |
| SLS | 1.5 | 0.45 | 0 | 0.00 |
| Total weight | 150 | 45 | 150 | 45.00 |

Coating: 4% w/w, Opadry White

In an additional study, residual solvent was evaluated in the tables wherein IPA was used as a granulation solvent. The results are provided below in Table 5.

TABLE 5

| Sample ID | Sample Weight (mg) | Reported Content (ppm) |
|---|---|---|
| P14K080002A | 108.84 | 387 |
| P14K080002B | 107.48 | 292 |
| P14K080003A | 100.35 | 1272 |
| P14K080003B | 102.15 | 470 |
| P14K080004A | 102.65 | 643 |
| P14K080004B | 102.90 | 164 |

The formulation screening strategy comprised a first batch screening under accelerated storage conditions at 40C/75% RH in open and closed containers. Another batch was screened under accelerated stress conditions at 60C in closed containers. Stability data is provided in Table 6.

TABLE 6

| | | Initial | | 1 Week 40° C./75% RH Open | | 1 Week 60° C. | |
|---|---|---|---|---|---|---|---|
| Sample Information | Composition | Assay, % | Total Impurity, % | Assay, % | Total Impurity, % | Assay, % | Total Impurity, % |
| P14K080001A | PVP/AC-Di-Sol/SLS | 98.6 | 0.436 | 98.9 | 0.602 | 90.6 | 2.157 |
| P14K080001B | PVP/Polyplasdone XL 10 | 101.4 | 0.334 | 94.1 | 2.673 | 101.1 | 2.629 |
| P14K080001C | PVP/AC-Di-Sol | 103.0 | 0.275 | 104.5 | 0.476 | 102.4 | 1.156 |
| P14K080001D | PVP/Polyplasdone XL 10/SLS | 107.6 | 0.370 | 104.2 | 1.002 | 107.6 | 2.082 |
| P14K080002A | Klucel LF/AC-Di-Sol/SLS | 106.9 | 0.222 | 107.8 | 0.210 | 105.0 | 1.653 |
| P14K080002B | Klucel LF/Polyplasdone XL 10 | 104.6 | 0.364 | 104.4 | 1.143 | 104.7 | 2.100 |
| P14K08002C | Klucel LF/AC-Di-Sol | 104.6 | 0.330 | 96.7 | 2.480 | 105.8 | 0.259 |
| P14K080002D | Klucel LF/Polyplasdone XL 10/SLS | 98.4 | 0.334 | 93.4 | 3.759 | 97.6 | 2.230 |

The analytical procedures for determination of content uniformity, blend uniformity, amount of active ingredient and related impurities (including degradation compounds) in pharmaceutical formulations of the present disclosure comprising active ingredient-containing tablets (5 mg, 20 mg and 50 mg strengths) comprised the use of an HPLC method. The column used for separation has USP L1 packing and dimensions of 4.6×150 mm, with a 3.5 micron particle size. The HPLC method uses gradient elution where the mobile phase was a buffer solution of 1 mM ammonium formate, pH 3.2, and 0.1% formic acid in acetonitrile, and eluted fractions were subject to UV detection at 275 nm. Detailed analytical results for prototype formulations at 1 week, 40C/75% RH in an open container are provided in Table 7.

TABLE 7

| 1 WK, 40° C./75% RH, Open | | | | | | |
|---|---|---|---|---|---|---|
| Batch # | Wt. of Tablets (g) | Impurities | Retention Time, min | RRT | Peak Area | % Recovery |
| P14K080002A | 1.60316 | Unknown-1 | 7.106 | 0.67 | 1258 | 0.002 |
| | | Unknown-2 | 7.399 | 0.70 | 2125 | 0.004 |
| | | Unknown-8 | 9.79 | 0.93 | 5716 | 0.011 |
| | | Unknown-10 | 10.315 | 0.98 | 7262 | 0.014 |
| | | ASN002 | 10.559 | 1.00 | 40910752 | N/A |
| | | Unknown-12 | 11.303 | 1.07 | 29691 | 0.061 |
| | | Unknown-13 | 11.593 | 1.10 | 21378 | 0.043 |
| | | Unknown-14 | 11.836 | 1.12 | 2951 | 0.006 |
| | | Unknown-15 | 12.187 | 1.15 | 4399 | 0.009 |
| | | Unknown-16 | 12.428 | 1.18 | 1716 | 0.003 |
| | | Unknown-17 | 12.771 | 1.21 | 5924 | 0.012 |
| | | Unknown-21 | 13.721 | 1.30 | 12305 | 0.025 |
| | | Unknown-25 | 14.568 | 1.38 | 2464 | 0.005 |

TABLE 7-continued

1 WK, 40° C./75% RH, Open

| Batch # | Wt. of Tablets (g) | Impurities | Retention Time, min | RRT | Peak Area | % Recovery |
|---|---|---|---|---|---|---|
| | | Unknown-26 | 14.86 | 1.41 | 1345 | 0.002 |
| | | Unknown-27 | 15.166 | 1.44 | 2264 | 0.004 |
| | | Unknown-36 | 18.288 | 1.73 | 4677 | 0.009 |
| | | % Total Impurity | | | | 0.210 |
| P14K080002B | 1.58841 | Unknown-2 | 7.388 | 0.70 | 2690 | 0.005 |
| | | Unknown-7 | 9.344 | 0.88 | 13003 | 0.026 |
| | | Unknown-8 | 9.769 | 0.93 | 8669 | 0.017 |
| | | Unknown-9 | 10.085 | 0.96 | 2400 | 0.004 |
| | | Unknown-10 | 10.294 | 0.97 | 14157 | 0.029 |
| | | ASN002 | 10.56 | 1.00 | 27284322 | N/A |
| | | Unknown-11 | 10.891 | 1.03 | 23904 | 0.049 |
| | | Unknown-12 | 11.302 | 1.07 | 402914 | 0.828 |
| | | Unknown-13 | 11.595 | 1.10 | 18407 | 0.037 |
| | | Unknown-14 | 11.841 | 1.12 | 2100 | 0.004 |
| | | Unknown-15 | 12.201 | 1.16 | 6897 | 0.014 |
| | | Unknown-16 | 12.432 | 1.18 | 3066 | 0.006 |
| | | Unknown-17 | 12.798 | 1.21 | 10370 | 0.021 |
| | | Unknown-18 | 13.078 | 1.24 | 5544 | 0.011 |
| | | Unknown-20 | 13.667 | 1.29 | 15836 | 0.032 |
| | | Unknown-25 | 14.628 | 1.39 | 6789 | 0.013 |
| | | Unknown-27 | 15.171 | 1.44 | 2786 | 0.005 |
| | | Unknown-30 | 16.521 | 1.56 | 1719 | 0.003 |
| | | Unknown-31 | 16.767 | 1.59 | 2345 | 0.004 |
| | | Unknown-35 | 18.071 | 1.71 | 5593 | 0.011 |
| | | Unknown-36 | 18.269 | 1.73 | 9928 | 0.020 |
| | | Unknown-38 | 19.189 | 1.82 | 2262 | 0.004 |
| | | % Total Impurity | | | | 1.143 |

The formulation batches described above were prepared by micronizing the active ingredient, combining the active ingredient with intragranular and extragranular components to form a tablet, and finally coating the tablet.

Micronization: The general procedure for micronizing the active ingredient comprised the use of a Micronizer 4" SDM and batches of approximately 500-550 g were micronized. The micronization parameters consisted of the following:
Inlet Air-100 PSI
Grinding Chamber Air-40 PSI
Feeder Nozzle-20 PSI
Number of Passes #1

In an embodiment, 512 g of material was added to the feeding chamber and the weight of the material obtained after micronization was 452 g.

The table below provides particle size measurement in hexane for the active ingredient as described herein.

TABLE 8A

| Active Ingredient | D(0.1) | D(0.5) | D(0.9) |
|---|---|---|---|
| As is API | 3.752 | 12.354 | 32.411 |
| Micronized API | 1.675 | 7.036 | 13.530 |

Figure 2:
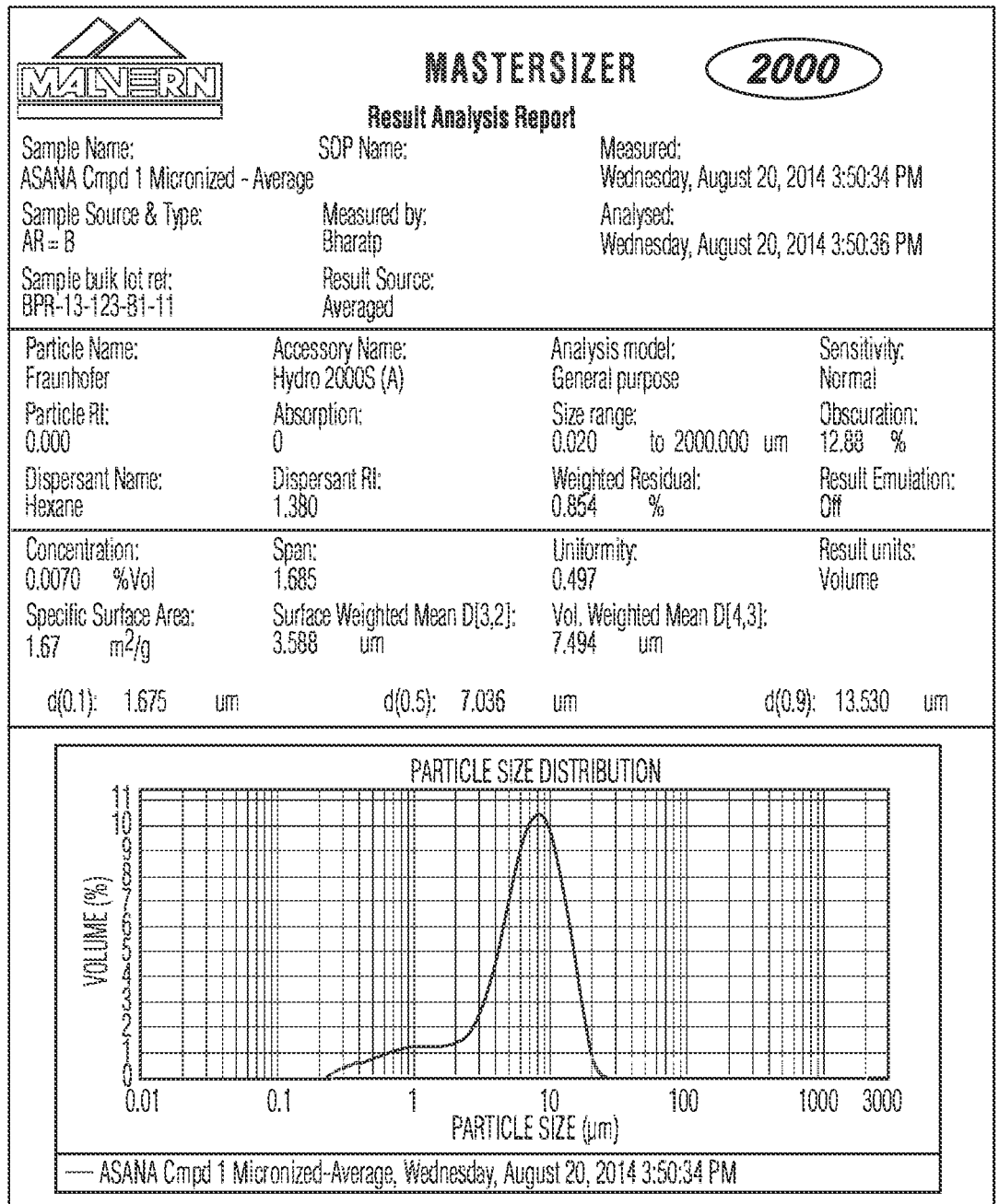
FIG. 2 provides a particle size distribution results analysis report for the active ingredient after micronization.

FIG. 1 provides a particle size distribution results analysis report for the active ingredient prior to micronization, and FIG. 2 provides a particle size distribution results analysis report for the active ingredient after micronization.

Formulation Configuration: The formulations were configured into two tablet formulations, 20 mg, and 50 mg. Table 8b provides the evaluation of residual solvent levels (isopropyl alcohol or "IPA") for the 20 mg tablet, and Table 8c provides PVP K30-IPA evaluation of IPA residual solvent levels for the 50 mg tablet. The general procedure for making the formulations comprised weighing the required intragranular material and mixing it, titurating the powder mixer in a mortar and pestle, slowing adding IPA-PVP K30 10% w/w solution to the powder while continuingly mixing (adding additional IPA 99% until granules are formed if required), drying the wet mass in an oven at 40C for 30 minutes, passing the dried mass through Fitzmill (Hammer Forward, Screen #0040, Speed #2500 RPM), weighing and measuring the required extragranular materials and adding them in following order Vivapur 101, Primellose/Polyplasone XL-10 and SLS, mixing for 3-5 minutes in a tubular mixer, adding magnesium stearate and mixing for 1 minute in a tubular mixer, tableting the formulation in F-Press keeping target at 150 mg and hardness at 9 KPa.

TABLE 8b

Evaluation of PVP K30-IPA

| Ingredients | Formulation A mg/tab | Batch (g) |
|---|---|---|
| Intragranular | | |
| API | 20 | 8.00 |
| Lactose Monohydrate | 102.25 | 40.90 |
| Primellose | 4.5 | 1.80 |
| Polyplasdone XL-10 | 0 | 0.00 |
| PVP K-30 | 4.5 | 1.80 |
| Extragranular | | |
| Vivapur 101 | 11.25 | 4.50 |
| Primellose | 4.5 | 1.80 |
| Polyplasdone XL-10 | 0 | 0.00 |

TABLE 8b-continued

Evaluation of PVP K30-IPA

| Ingredients | Formulation A mg/tab | Batch (g) |
|---|---|---|
| Magnesium Stearate | 1.5 | 0.60 |
| SLS | 1.5 | 0.60 |
| Total weight | 150 | 60 |

TABLE 8c

Evaluation of PVP K30-IPA

| Ingredients | Formulation A mg/tab | Batch (g) |
|---|---|---|
| Intragranular | | |
| API | 50 | 20.00 |
| Lactose Monohydrate | 72.25 | 28.90 |
| Primellose | 4.5 | 1.80 |
| Polyplasdone XL-10 | 0 | 0.00 |
| PVP K-30 | 4.5 | 1.80 |
| Extragranular | | |
| Vivapur 101 | 11.25 | 4.50 |
| Primellose | 4.5 | 1.80 |
| Polyplasdone XL-10 | 0 | 0.00 |
| Magnesium Stearate | 1.5 | 0.60 |
| SLS | 1.5 | 0.60 |
| Total weight | 150 | 60 |

The coating formula is provided below in Table 8d:

TABLE 8d

| # | Mg per Dose | % w/w | Ingredients | Theoretical (g) |
|---|---|---|---|---|
| 1 | 150 | n/a | API tablets | 300 |
| 2 | 6 | 4 | Opadry White 03F180004 | 12 |
| 3 | n/a | n/a | Purified Water | 54 |
| 4 | n/a | n/a | Isopropyl Alcoholo 99% | 54 |

Stability data was generated and collected for eight prototype formulations. Details of the study results are proved below in Table 9a (40 degrees Celsius/75RH) and Table 9b (60 degrees Celsius). Formulations 1A, 1C, 2A and 2C displayed superior stability results.

TABLE 9a

| Formulation | Total impurity % | Selection |
|---|---|---|
| 1A | 0.6 | ✓ |
| 1B | 2.6 | |
| 1C | 0.47 | ✓ |
| 1D | 1.0 | |
| 2A | 0.21 | ✓ |
| 2B | 1.1 | |
| 2C | 2.5 | |
| 2D | 3.8 | |

TABLE 9b

| Formulation | Total impurity % | Selection |
|---|---|---|
| 1A | 2.2 | |
| 1B | 2.6 | |
| 1C | 1.2 | |
| 1D | 2.1 | |
| 2A | 1.6 | |
| 2B | 2.1 | |
| 2C | 0.26 | ✓ |
| 2D | 2.26 | |

Formulations 1A, 1C, 2A and 2C were further evaluated to test the effect of antioxidants.

As shown in Tables 10a and 10b, certain prototype formulations were evaluated for determination of DL-α-Tocopherol (Vitamin E) content comprising an HPLC method. The column used for separation has a USP L1 packing, 4.6×150 mm, with a 3.5 micron particle size, and method uses isocratic elution with water and acetonitrile (97:3 v/v) as the mobile phase and UV detection at 294 nm.

TABLE 10a

Evaluation of PVP K30 -IPA/Alpha Tocopherol BATCH #P14K080006

| Ingredients | Formulation A mg/tab | Formulation B mg/tab |
|---|---|---|
| Intragranular | | |
| API | 5 | 5 |
| Lactose Monohydrate | 117.15 | 116.95 |
| Primellose | 4.5 | 4.5 |
| PVP K 30 | 4.5 | 4.5 |
| Alpha Tocopherol | 0.1 | 0.3 |
| Extragranular | | |
| Vivapur 101 | 11.25 | 11.25 |
| Primellose | 4.5 | 4.5 |
| Magnesium Stearate | 1.5 | 1.5 |
| SLS | 1.5 | 1.5 |
| Total weight | 150 | 150 |

TABLE 10b

Evaluation of Klucel LF -IPA/Alpha Tocopherol BATCH #P14K080007

| Ingredients | Formulation A mg/tab | Formulation B mg/tab |
|---|---|---|
| Intragranular | | |
| API | 5 | 5 |
| Lactose Monohydrate | 117.15 | 116.95 |
| Primellose | 4.5 | 4.5 |
| Klucel LF | 4.5 | 4.5 |
| Alpha Tocopherol | 0.1 | 0.3 |
| Extragranular | | |
| Vivapur 101 | 11.25 | 11.25 |
| Primellose | 4.5 | 4.5 |
| Magnesium Stearate | 1.5 | 1.5 |
| SLS | 1.5 | 1.5 |
| Total weight | 150 | 150 |

Further analysis was conducted to evaluate excipient compatibility, stability and disintegration at the 5 mg strength: Ac-Di-Sol and Polyplasdone XL-10; PVP KI-30 and Klucel LF; and SLS. In addition, higher strength tablets were evaluated for stability and tablet properties, the effect of antioxidants (5 mg strength), and polymorphs. Formulations A, B, C, and D provided in Table 11 below were selected for further evaluation.

TABLE 11

| Ingredients | Formulation A mg/tab | Batch (g) | Formulation B mg/tab | Batch (g) |
|---|---|---|---|---|
| *Intragranular* | | | | |
| API | 5 | 1.50 | 5 | 1.50 |
| Lactose Monohydrate | 117.25 | 35.18 | 118.75 | 35.63 |
| Primellose | 4.5 | 1.35 | 0 | 0.00 |
| Polyplasdone XL-10 | 0 | 0.00 | 4.5 | 1.35 |
| Klucel LF | 4.5 | 1.35 | 4.5 | 1.35 |
| *Extragranular* | | | | |
| Vivapur 101 | 11.25 | 3.38 | 11.25 | 3.38 |
| Primellose | 4.5 | 1.35 | 0 | 0.00 |
| Polyplasdone XL-10 | 0 | 0.00 | 4.5 | 1.35 |
| Magnesium Stearate | 1.5 | 0.45 | 1.5 | 0.45 |
| SLS | 1.5 | 0.45 | 0 | 0.00 |
| Total weight | 150 | 45 | 150 | 45.00 |

| Ingredients | Formulation C mg/tab | Batch (g) | Formulation D mg/tab | Batch (g) |
|---|---|---|---|---|
| *Intragranular* | | | | |
| API | 5 | 1.50 | 5 | 1.50 |
| Lactose Monohydrate | 118.75 | 35.63 | 117.25 | 35.18 |
| Primellose | 4.5 | 1.35 | 0 | 0.00 |
| Polyplasdone XL-10 | 0 | 0.00 | 4.5 | 1.35 |
| Klucel LF | 4.5 | 1.35 | 4.5 | 1.35 |
| *Extragranular* | | | | |
| Vivapur 101 | 11.25 | 3.38 | 11.25 | 3.38 |
| Primellose | 4.5 | 1.35 | 0 | 0.00 |
| Polyplasdone XL-10 | 0 | 0.00 | 4.5 | 1.35 |
| Magnesium Stearate | 1.5 | 0.45 | 1.5 | 0.45 |
| SLS | 0 | 0.00 | 1.5 | 0.45 |
| Total weight | 150 | 45 | 150 | 45.00 |

Following additional analysis, the following formulations (Table 12) were selected as lead candidates:

TABLE 12

| Ingredients | Formulation A mg/tab | Batch (g) |
|---|---|---|
| *Intragranular* | | |
| API | 5 | 1.50 |
| Lactose Monohydrate | 117.25 | 35.18 |
| Primellose | 4.5 | 1.35 |
| Polyplasdone XL-10 | 0 | 0.00 |
| Klucel LF | 4.5 | 1.35 |
| *Extragranular* | | |
| Vivapur 101 | 11.25 | 3.38 |
| Primellose | 4.5 | 1.35 |
| Polyplasdone XL-10 | 0 | 0.00 |
| Magnesium Stearate | 1.5 | 0.45 |
| SLS | 1.5 | 0.45 |
| Total weight | 150 | 45 |

| | P14080002A | | |
|---|---|---|---|
| Sample Information | Assay, % | Total Impurity, % | Single Largest Impurity, % (RRT = 1.07) |
| Initial | 106.9 | 0.222 | 0.055 |
| 1 Week 40° C./75% RH Open | 107.8 | 0.210 | 0.061 |
| 1 Week 60° C. | 105.0 | 1.653 | 1.181 |
| 2 Week 40° C./75% RH Open | 102.5 | 0.257 | 0.064 |
| 2 Week 40° C./75% RH Closed | 105.6 | 0.313 | 0.122 |
| 4 Week 40° C./75% RH Closed | 103.5 | 0.455 | 0.128 |

| Ingredients | Formulation C mg/tab | Batch (g) |
|---|---|---|
| *Intragranular* | | |
| API | 5 | 1.50 |
| Lactose Monohydrate | 118.25 | 35.63 |
| Primellose | 4.5 | 1.35 |
| Polyplasdone XL-10 | 0 | 0.00 |
| Klucel LF | 4.5 | 1.35 |
| *Extragranular* | | |
| Vivapur 101 | 11.25 | 3.38 |
| Primellose | 4.5 | 1.35 |
| Polyplasdone XL-10 | 0 | 0.00 |
| Magnesium Stearate | 1.5 | 0.45 |
| SLS | 0 | 0.00 |
| Total weight | 150 | 45 |

| | P14080002C | | |
|---|---|---|---|
| Sample Information | Assay, % | Total Impurity, % | Single Largest Impurity, % (RRT = 1.07) |
| Initial | 104.6 | 0.330 | 0.144 |
| 1 Week 40° C./75% RH Open | 98.7 | 0.313 | 0.115 |
| 1 Week 60° C. | 105.8 | 0.259 | 0.095 |
| 2 Week 40° C./75% RH Open | 102.8 | 0.265 | 0.100 |
| 2 Week 40° C./75% RH Closed | 101.5 | 0.358 | 0.074 |
| 4 Week 40° C./75% RH Closed | 90.1 | 0.178 | 0.017 (not largest) |

Example 2

Immediate-Release Formulations

Immediate-release formulations of the disclosure containing a micronized hydrochloride salt of the active ingredient described herein were prepared in 2 dosage strengths (5 mg and 20 mg) for use in clinical studies. Table 13 provides component composition and amounts for 5 mg and 20 mg strength tablets.

TABLE 13

| | Amount per Tablet (mg) | |
|---|---|---|
| Component | 5 mg | 20 mg |
| Compound 1 HCl (micronized) | 5.396** | 21.584** |
| Lactose Monohydrate, NF (Modified Spray Dried Fast | 116.704 | 100.516 |
| Hydroxypropyl Cellulose, NF (Klucel ELF Pharm) | 4.500 | 4.500 |
| Croscarmellose Sodium, NF (Ac-Di-Sol) | 9.000 | 9.00 |
| Vitamin E, USP (dl-α- Tocopherol) | 0.150 | 0.150 |
| Microcrystalline Cellulose, NF (Vivapur Type 101) | 11.250 | 11.250 |
| Sodium lauryl sulfate, NF (Kolliphor SLS fine) | 1.500 | 1.500 |
| Magnesium Stearate, NF (Ligamed MF-2-K) | 1.500 | 1.500 |
| Isopropyl Alcohol, USP* | — | — |
| Core Tablet | 150.00 | 150.00 |
| Opadry White 03F180004 | 6.000 | 6.000 |

TABLE 13-continued

|  | Amount per Tablet (mg) | |
|---|---|---|
| Component | 5 mg | 20 mg |
| Purified Water* | — | — |
| Isopropyl alcohol* | — | — |
| Total Weight (mg) | 156.00 | 156.00 |

USP = United States Pharmacopeia;
NF = National Formulary
*Evaporates during the process
**Weights of Compound 1 hydrochloride include correction factors for purity and hydrogen chloride content of API such that the weights of Compound 1 free base in 5 mg and 20 mg tablets are 5 mg and 20 mg per tablet, respectively.

The formulations provided in Table 13 further comprise inactive ingredients as provided below in Table 14. Each excipient is within the potency limits listed for an oral route of administration in the most current FDA Inactive Ingredient Guide (IIG) as applicable. Table 15 provides the quantitative composition of Opadry White 03F180004.

TABLE 14

|  | Amount per Tablet (mg) | | IIG limits | Component |
|---|---|---|---|---|
| Components | 5 mg | 20 mg | (Mg) | Function |
| Lactose Monohydrate, NF (Modified Spray dried fast Flo) | 116.704 | 100.516 | 587.44 | Diluent |
| Hydroxypropyl Cellulose, NF (Klucel ELF Pharm) | 4.50 | 4.50 | 240 | Binder |
| Croscarmellose Sodium, NF (AC-DI-SOL) | 9.00 | 9.00 | 180 | Disintegrant |
| Vitamin E, USP (dl-α-Tocopherol) | 0.15 | 0.15 | 1.34 | Antioxidant |
| Microcrystalline Cellulose, NF (Vivapur Type 101) | 11.25 | 11.25 | 234.6 | Diluent |
| Sodium Lauryl Sulfate, NF (Kolliphor SLS fine) | 1.50 | 1.50 | 51.69 | Wetting agent |
| Magnesium Stearate, NF (Ligamed MF-2-K) | 1.50 | 1.50 | 400.748 | Lubricant |
| Isopropyl Alcohol, USP* | — | — | — | Granulation solvent |
| Opadry White 03F180004 | 6.00 | 6.00 | See Table 3 for the break down | Aesthetic Coating system |
| Purified Water * | — | — | — | Coating solvent |
| Isopropyl Alcohol, USP* | — | — | — | Coating solvent |

TABLE 15

| Ingredients/Compendial Reference | IIG limits (mg) | Blend formula (% w/w) | Amount (mg/tablet) | |
|---|---|---|---|---|
|  |  |  | 5 mg | 20 mg |
| HPMC 2910/Hypromellose (USP, PhEur, JP) | 92.794 | 60.00 | 3.6 | 3.6 |
| Titanium Dioxide (USP, FCC, PhEur, JP) | 35.7 | 20.00 | 1.2 | 1.2 |
| Talc (USP, FCC, PhEur, JP) | 220.4 | 10.00 | 0.6 | 0.6 |
| Macrogol/PEG (NF, FCC, JECFA, Ph. Eur) MW 6000 | 450 | 10.00 | 0.6 | 0.6 |
| Total weight of Opadry White 03F180004 per tablet |  |  | 6 mg | 6 mg |

The above-described tablets are packaged into high density polyethylene (HDPE) bottles with induction seals and packed with 1 g silica gel desiccant canisters, closed with child-resistant polypropylene screw caps.

Example 3

Evaluation of Clinical Activity, Safety and Tolerability of Compound 1, a Dual SYK/JAK Inhibitor, Inpatients with Moderate to Severe Atopic Dermatitis Example 3 evaluates the safety, tolerability and efficacy of Compound 1 in subjects with moderate to severe atopic dermatitis, as well as the pharmacokinetic (PK) profile of Compound 1 and pharmacodyncamic/biomarkers for evidence of drug activity.

Methods and Study Design:

The study conducted was a randomized, double-blind, placebo-controlled, multicenter, sequential dose escalation study in subjects with moderate-to severe atopic dermatitis. The study included a screening period (up to 30 days) and a treatment period for 4 weeks with a 14 day follow up period that concluded with an end-of-study visit. Three sequential cohorts of 20, 40 and 80 mg QD were evaluated. At each dose level a total of 12 subjects were enrolled with 9 subjects receiving Compound 1, and 3 subjects receiving matching placebos.

A total of approximately 36 subjects were randomized at approximately 10 study sites in the U.S. and Canada. Dose escalation occurred after a review of the blinded safety data by a Safety Review Committee (SRC). Dose escalation continues until the Maximum Tolerated Dose (MTD) is defined. The dose at which study drug related adverse events within the same organ class results in treatment discontinuation in ≥2 of the subjects (or ≥3 subjects in any system organ class), is considered to exceed the Maximum Tolerated Dose (MTD).

The dose level immediately below is considered the MTD. All data up to and including the assessments at the end of the 28-day treatment period (Day 29) of the current cohort were included in the review. The SRC reviews the blinded safety data and recommends initiation of the next dose cohort or halting dose escalation. Lower or intermediate dose levels and alternate dosing schedules other than those proposed, may be explored as supported by the clinical data of the previous cohort(s) in an effort to better define the MTD. Higher dose levels may be evaluated as supported by the emerging clinical data.

Upon signing the informed consent, the each subject underwent screening assessments from Day −30 to Day −1 prior to study drug administration. On Day 1 (baseline), eligible subjects were randomized, subjected to the Day 1/baseline assessments and received Compound 1 at 20, 40 or 80 mg or placebo, dependent on cohort and randomization schedule. At this visit, PK/PD samples were collected at predose and up to 8 hours (or up to 12 hours at selected sites). Subjects were monitored in clinic for 2 hours following the first study drug administration. Subjects returned to the clinic on Day 2 for PK and PD samples (24 hours post dose).

Pre-dose PK and PD samples were collected on Days 8 and 29 (last day of treatment). On Day 15, PK/PD samples were also collected at pre-dose and up to 8 hours post-dose and subjects returned on Day 16 for PK and PD samples (24 hours post dose). Subjects came in for additional safety assessments on Days 8, 22 and 29, as well as at the end of the follow up period (Day 43). Disease assessments were conducted on Days 1, Day 15 and Day 29.

Figures 5, 6:
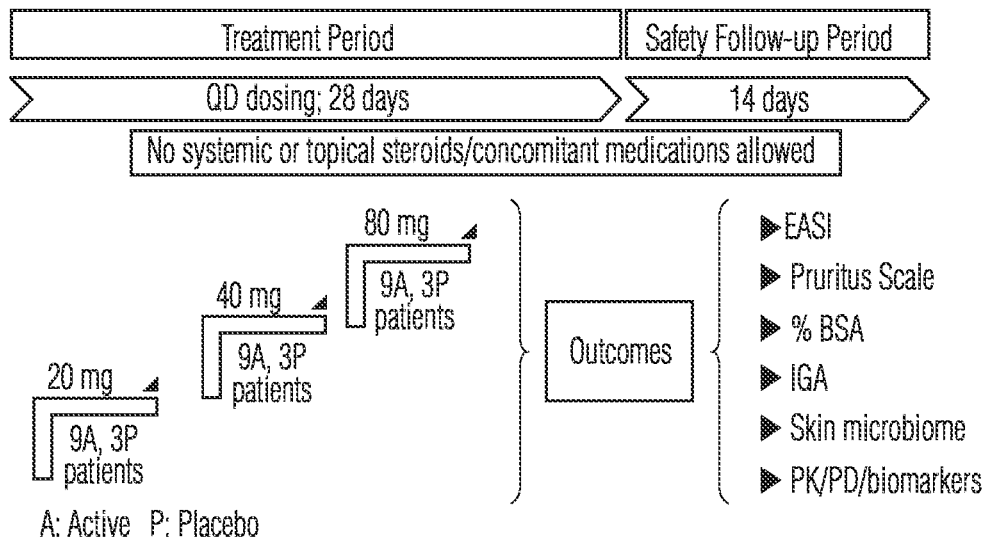
FIG. 5 is a graphical illustration of the study design of Example 3.
FIG. 6 is a graphical illustration of the patient demographics of Example 3.

FIG. 5 is a graphical illustration of the study design, including the treatment period, safety follow-up period, starting doses and number of subjects. In the study design shown in FIG. 5, 9 active and 3 placebo subjects were randomized in each Cohort. FIG. 6 is a graphical illustration of the patient demographics. In the demographics shown in FIG. 6, there were no use of topical or systemic steroids, and emollient use was required with consistent application (once daily or twice daily).

Diagnosis and Subject Inclusion Exclusion Criteria:
Inclusion Criteria:
1. Ability to provide written informed consent obtained prior to any study-related procedure being performed.
2. Male or female, 18≤ years and ≤75 years of age.
3. Chronic AD diagnosed by the Hanifin and Rajka criteria that has been present for at least 6 months before the screening visit (information obtained from medical chart or patient history).
4. Eczema Area and Severity Index (EASI) score ≥16 at baseline visits.
5. Investigator's Global Assessment (IGA) score ≥3 at the baseline visits.
6. At least 10% body surface area (BSA) of AD involvement at the baseline visits.
7. Subject has a body mass index (BMI)≤35 kg/m$^2$.
8. History of inadequate response to topical corticosteroids or calcineurin inhibitors as treatment for AD within 1 year before the screening visit (information obtained from medical chart or patient history).
9. Subjects must apply stable doses of an Investigator approved, basic bland emollient once or twice-daily for at least 7 days before the baseline visit.
10. Subjects must be willing to use medically effective methods of birth control, if of reproductive potential* and sexually active (unless they are exclusively sexually active with same-sex partners). Adequate birth control is defined as agreement to consistently practice an effective and accepted method of contraception from at least 4 weeks prior to baseline (Day 1) throughout the duration of the study and for 4 weeks after last dose of study drug:

a. For females, adequate birth control methods are defined as: hormonal contraceptives, intrauterine device (IUD), vasectomized partner or double barrier contraception (i.e., condom+diaphragm, condom or diaphragm+spermicidal gel or foam).
b. For males, adequate birth control methods are defined as: vasectomy, double barrier contraception (i.e., condom+diaphragm, condom or diaphragm+spermicidal gel or foam) or used by the sole partner of a hormonal contraceptive or IUD.

For females, menopause is defined as 24 months without menses; if in question, a follicle-stimulating hormone confirming the nonchildbearing potential (refer to laboratory reference ranges for confirmatory level) must be documented prior to baseline visit. Hysterectomy, bilateral oophorectomy, bilateral salpingectomy, or bilateral tubal ligation must be documented, as applicable.

11. Females of reproductive potential must have a negative serum pregnancy test at screening and negative urine pregnancy test at baseline (Day 0).
12. Subjects must be willing and able to comply with clinic visits and study-related procedures Exclusion Criteria:
1. Subjects have clinically infected atopic dermatitis.
2. Presence of any of the following laboratory abnormalities at the screening visit:
   a. Hemoglobin <11 g/dL
   b. White blood cell (WBC)<3.0×10$^3$/μL
   c. Platelet count <125×10$^3$/μL
   d. Neutrophils <2.50×10$^3$/μL
   e. Lymphocytes <1.2×10$^3$/μL
   f. Aspartate aminotransferase (AST)/alanine aminotransferase (ALT) >1.5×the upper limit of normal (ULN)
   g. Total bilirubin >ULN (except for elevated indirect bilirubin secondary to Gilbert's syndrome)
   h. Creatinine >ULN.
3. Subjects with uncontrolled hypertension within the last 1 month prior to screening or blood pressure at screening of systolic blood pressure >140 mm Hg or diastolic BP >90 mm Hg, confirmed by repeat assessments.
4. Positive QuantiFERON®-TB test indicating possible tuberculosis infection, unless there is documented evidence of a completed adequate treatment course for latent TB.
5. History of latent or active tuberculosis or exposure to endemic areas within 8 weeks.
6. Availability of chest radiograph at screening or within 3 months before the screening visit (radiology report must be available) with results consistent with prior TB infection (including but not limited to apical scarring, apical fibrosis, or multiple calcified granuloma). This does not include non-caseating granulomata. Screening chest radiography is not mandatory if no clinical signs or symptoms indicating active TB infection, unless history of latent or active tuberculosis or exposure to endemic areas within the last 12 months.
7. Positive hepatitis B core antigen, positive hepatitis B surface antigen, positive hepatitis C antibody, and/or positive human immunodeficiency virus at the screening visit.
8. Subject has used hydroxyzine or diphenhydramine within 1 week prior to baseline (Day 1).
9. Subject has used topical products containing urea within 1 week prior to baseline (Day 1).

10. Subject has used systemic antibiotics within 2 weeks or topical antibiotics within 1 week prior to baseline (Day 1).
11. Subject has used any topical medicated treatment for atopic dermatitis within 2 weeks prior to baseline (Day 1), including, but not limited to, topical corticosteroids, calcineurin inhibitors, tars, bleach, antimicrobials, medical devices, and bleach baths.
12. Subject has used systemic treatments (other than biologics) that could affect atopic dermatitis less than 4 weeks prior to baseline (Day 1) (e.g., retinoids, calcineurin inhibitors, methotrexate, cyclosporine, hydroxycarbamide [hydroxyurea], azathioprine, oral/injectable corticosteroids). Note: Intranasal corticosteroids, eye drops containing corticosteroids, and inhaled corticosteroids for stable medical conditions are allowed if subject has been on a stable dose for at least 4 weeks prior to baseline (Day 1) and will continue usage at the same dose for the duration of the study.
13. Subject has received any marketed or investigational biological agent within 12 weeks or 5 half-lives (whichever is longer) prior to baseline (Day 1).
14. Subject is currently receiving a non-biological investigational product or device or has received one within 4 weeks prior to baseline (Day 1).
15. Subject has excessive sun exposure, is planning a trip to a sunny climate, or has used tanning booths within 4 weeks prior to baseline (Day 1), or is not willing to minimize natural and artificial sunlight exposure during the study. Use of sunscreen products and protective apparel are recommended when exposure cannot be avoided.
16. Subject has received a live attenuated vaccine within 4 weeks prior to baseline (Day 1) or plans to receive a live attenuated vaccine during the study and up to 4 weeks or 5 half-lives (of the study product), whichever is longer, after the last study product administration.
17. Subject is known to have immune deficiency or is immunocompromised.
18. History of malignancy within 5 years before the baseline visit, with the following exceptions:
   a. subjects with a history of completely treated carcinoma in situ of cervix, and non-metastatic squamous or basal cell carcinoma of the skin are allowed.
19. Planned major surgical procedure during the length of the patient's participation in this study.
20. History of congestive heart failure New York Heart Association (NYHA) class III or IV
21. 12-Lead electrocardiogram (ECG) abnormalities considered by the investigator to be clinically significant or QTc F≥450 milliseconds, regardless of clinical significance, at screening. Abnormal ECG may be confirmed with one repeat assessment. For subjects with QTcF≥450 msec on initial ECG, the mean of the two QTc F assessments will determine eligibility.
22. Myocardial infarction, angioplasty, or cardiac stent placement within the last 6 months.
23. A medical condition requiring the therapeutic use of anticoagulants NSAID (Nonsteroidal Antiinflammatory Drugs) and low-dose aspirin will be not considered antiplatelets.
24. History of hypertrophic scarring or keloid formation in scars or suture sites.
25. Has difficulty swallowing medications, or known history of malabsorption syndrome.
26. History of recurrent GERD (Gastroesophageal reflux disease) requiring the use of proton pump inhibitors within the last month.
27. Known history of diverticulitis.
28. Uncontrolled diabetes.
29. Any medical or psychiatric condition which, in the opinion of the investigator or the sponsor's medical monitor, would place the patient at risk, interfere with participation in the study, or interfere with the interpretation of study results.
30. Pregnant or breast-feeding women.
31. Known hypersensitivity to Compound 1 or its excipients.
32. Prior treatment with SYK or JAK inhibitors for which the subject received no clinical benefit, or the subject relapsed whilst on therapy.

Investigational Product, Dosage and Mode of Administration:

Compound 1 was administered orally at doses of 20, 40 and 80 mg qd. Compound 1 was made available in 5-mg, 20-mg, and 50-mg strength tablets.

Duration of Study:

The total treatment period for each patient was 4 weeks (to day 29) and the total follow-up period for each patient was 14 days (to day 43).

Criteria for Evaluation:

Assessment of safety: Safety was assessed by AEs, vital signs, 12-lead ECG, physical examination, and laboratory safety assessments.

Assessment of PK variables: The following PK parameters for Compound 1 were derived from the concentration-time data of Compound 1 after the first and Day 15 dose administration in the fasted state, as data allowed: Cmax, tmax, $AUC_{0-\infty}$, $AUC_{0-t}$, AUC0-24, $\lambda z$, $t_{1/2}$, CL/F and Vd/F Assessment of efficacy variables: Preliminary efficacy was assessed by changes in the following assessments between Day 1 (baseline) and Days 15 and 29: IGA, EASI, 5-D Pruritus scale, Pruritus Numeric Rating Scale, % BSA involvement of AD, and skin microbiome analysis Assessment of Pharmacodynamics/Biomarker Parameters:
1. Change from baseline in inflammatory markers in serum (including immune markers and CRP)
2. Change from baseline in molecular skin biomarkers (inflammatory and barrier)
3. Change from baseline in cellular markers (including reduction in inflammatory cells)
4. Change from baseline in epidermal thickness and barrier markers in skin biopsies.

Assessments of Efficacy

Investigator's Global Assessment

The IGA is an assessment scale used in clinical studies to determine severity of AD and clinical response to treatment based on a 5-point scale ranging from 0 (clear) to 4 (severe) (18). The IGA score was assessed at screening, day 1/baseline (pre-dose), and days 15, 29, 43 or early termination.

TABLE 16

IGA assessment scale

| Score | Category | Definition |
|---|---|---|
| 0 | Clear | Minor, residual discoloration; no erythema or induration/papulation; no oozing/crusting |
| 1 | Almost clear | Trace, faint pink erythema with almost no induration/papulation; no oozing/crusting |

TABLE 16-continued

IGA assessment scale

| Score | Category | Definition |
|---|---|---|
| 2 | Mild disease | Faint pink erythema with mild induration/papulation; no oozing/crusting |
| 3 | Moderate disease | Pink-red erythema with moderate induration/papulation; there may be some oozing/crusting |
| 4 | Severe disease | Deep/bright red erythema with severe induration/papulation; with oozing/crusting |

5-D Pruritus Scale:

The 5-D Pruritus Scale is a 1-page, 5-question, validated questionnaire used in clinical trials to assess 5 dimensions of background itch: degree, duration, direction, disability, and distribution (19). Each question corresponds to 1 of the 5 dimensions of itch; subjects rate their symptoms over the preceding 2-week period as "present" or on a 1 to 5 scale, with 5 being the most affected. Subjects were subjected to this assessment at the following visits: day 1/baseline (pre-dose), and days 15, 29, 43 or early termination. The 5-D Pruritus Scale is provided in FIG. 3.

Pruritus Numeric Rating Scale:

The Pruritus NRS is a single-question assessment tool that is used to assess the patient's worst itch as a result of AD in the previous 12 hours. Subjects complete the patient recorded outcome once daily. Patient compliance on the pruritus NRS is followed at each clinic visit. Subjects were instructed on daily reporting at the Baseline visit and are queried for compliance at every clinic visit. Subjects completed the rating scale daily through the last study visit using the scale provided below.

| Numeric Rating Scale (NRS) | | | | | | | | | | |
|---|---|---|---|---|---|---|---|---|---|---|
| 0 | 1 | 2 | 3 | 4 | 5 | 6 | 7 | 8 | 9 | 10 |

No itch to worst imaginable itch

Eczema Area and Severity Index:

The Eczema Area and Severity Index (EASI) is a validated measure used in clinical practice and clinical trials to assess the severity and extent of AD. Four AD disease characteristics are assessed for severity by the investigator or designee on a scale of "0" (None) through "3" (severe). In addition, the area of AD involvement is assessed as a percentage by body area of head, trunk, upper and lower extremities and converted to a score of 0 to 6. Subjects were subjected to this assessment at the following visits: screening, day 1/baseline (pre-dose), and days 15, 29, 43 or early termination. The EASI assessment tool is provided in FIG. 4.

Body Surface Area Involvement of Atopic Dermatitis

Body surface area affected by AD was assessed for each major section of the body (head, trunk, arms, and legs) and is reported as a percentage of all major body sections combined. Subjects were subjected to this assessment at the following visits: screening, day1/baseline (pre-dose), and days 15, 29, 43 or early termination.

Skin Microbiome Analysis

Collection of skin microbiome samples is a non-invasive procedure where a swab is passed along the lesional surface of the area of worst eczema involvement, and another swab is passed along a non-lesional area of skin within 5 cm of the lesional site. Samples were collected from the same lesional and non-lesional areas at day 1/baseline (pre-dose) and days 29, 43 or early termination.

Assessment of Pharmacodynamic and Exploratory Biomarkers

Assessment of Exploratory Markers

Skin Biopsies:

For each subject, a maximum of four skin biopsies were collected during this study. Two punch biopsy samples (one from lesional skin and one from non-lesional skin) were collected at Day 1 and one punch biopsy was collected from the same lesional skin (outside the scar of the previous biopsies) at Day 15 (optional for subjects) and Day 29.

Figure 7A:
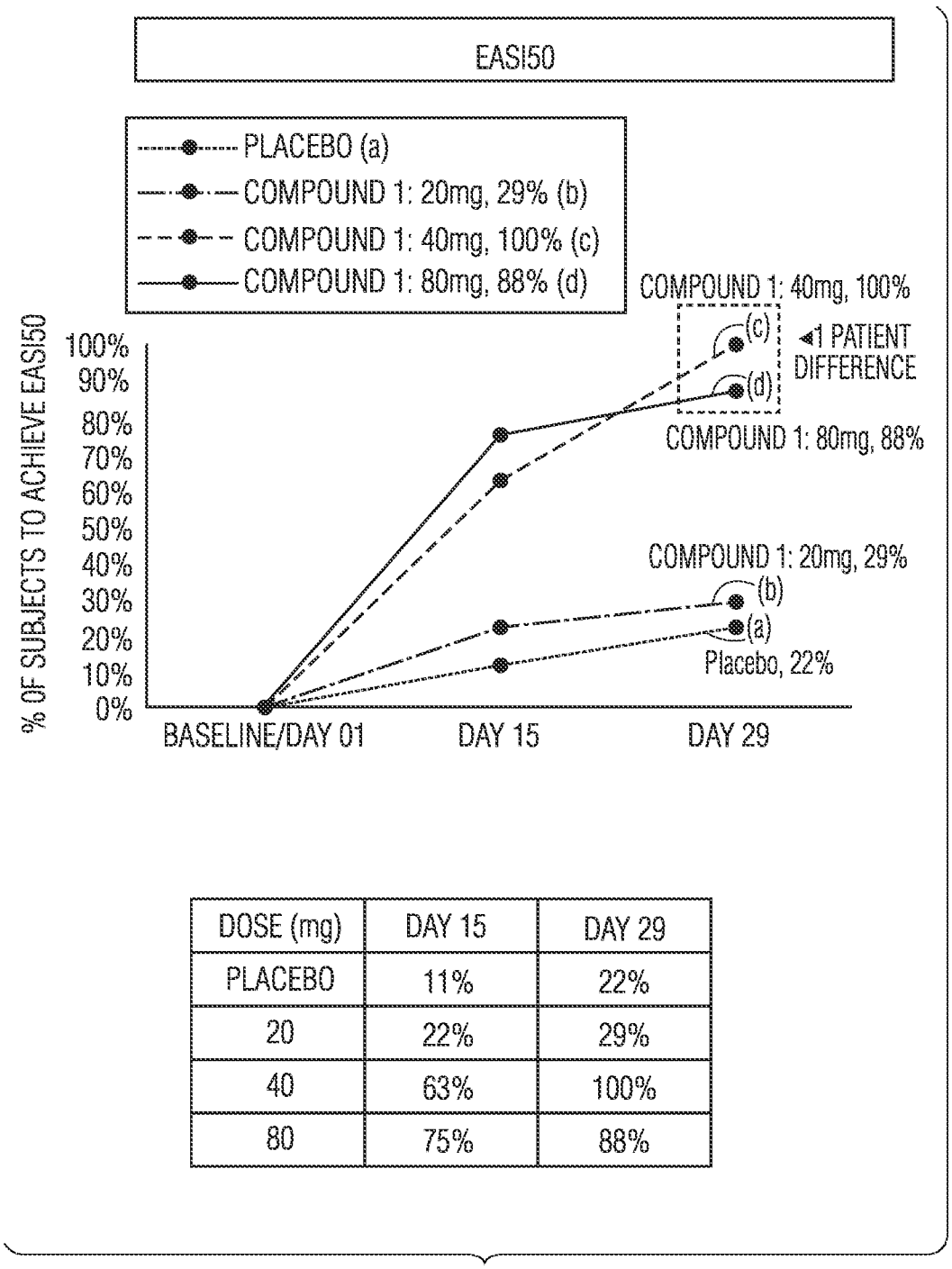
FIG. 7A is a graph of the % of subjects to achieve EASI50 over time (Day 1 to Day 29) for a placebo and Compound 1 in the doses of 20 mg, 40 mg and 80 mg, as demonstrated in Example 3.
Figure 7B:
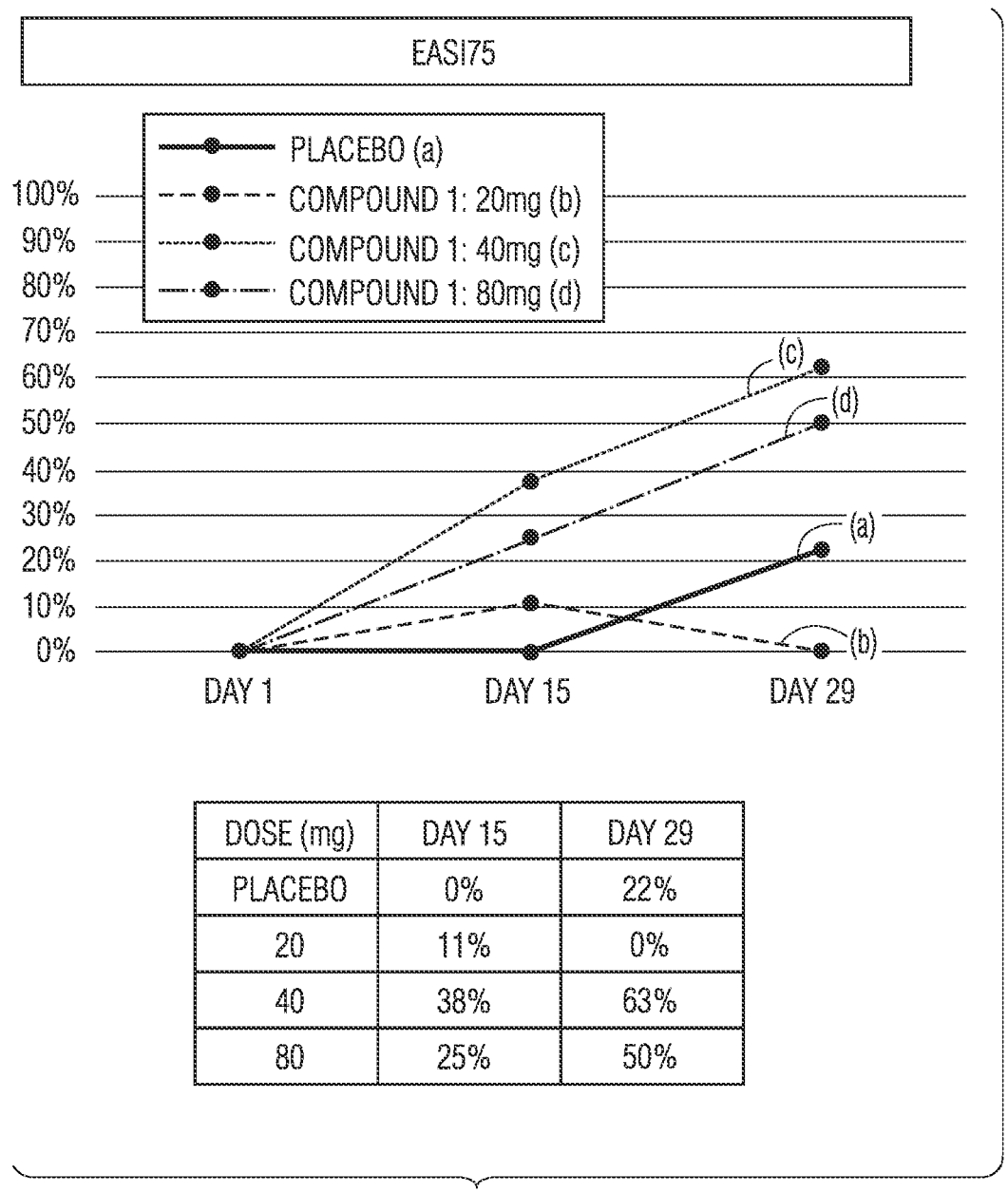
FIG. 7B is a graph of the % of subjects to achieve EASI75 over time (Day 1 to Day 29) for a placebo and Compound 1 in the doses of 20 mg, 40 mg and 80 mg, as demonstrated in Example 3.
Figures 9, 10:
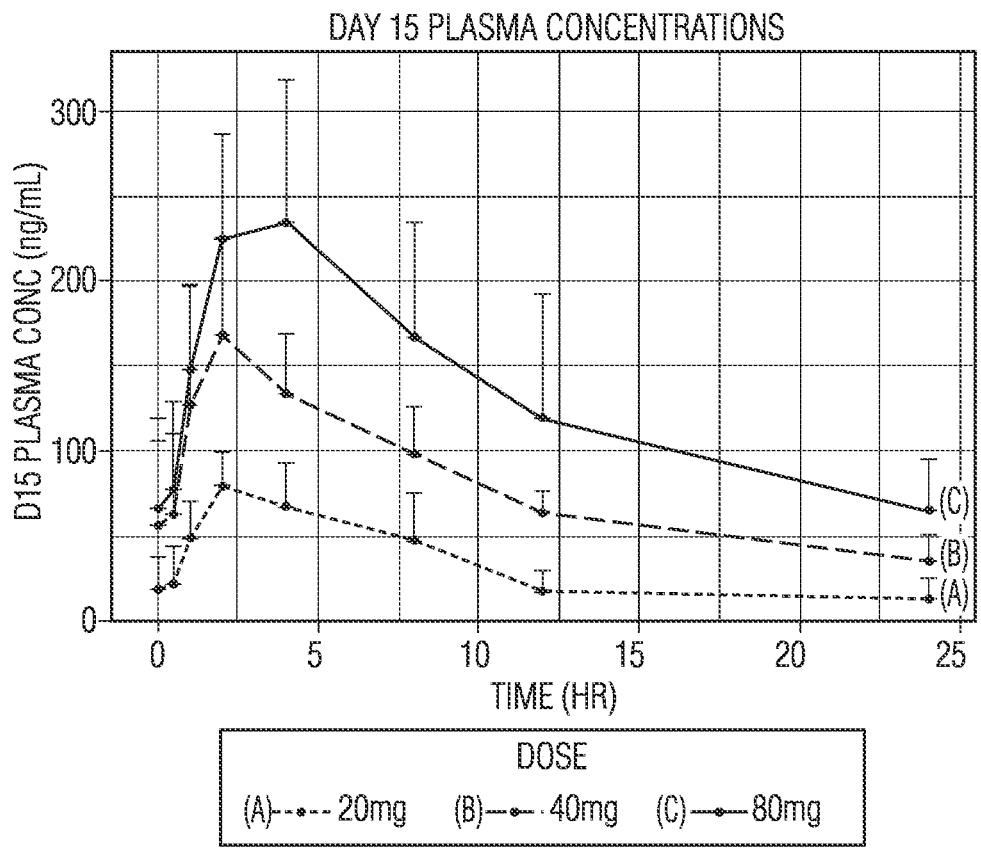
FIG. 9 is a graph of day 15 plasma concentration for Compound 1 in the doses of 20 mg, 40 mg and 80 mg, as demonstrated in Example 3.
FIG. 10 is a chart showing the inhibition of JAK and Syk kinase activity by Compound 1, Tofacitinib, Upadacitinib, and Baricitinib, as demonstrated in Example 3.

Other Biomarkers:

A panel of biological markers were assessed to determine the effect of Compound 1 on the disease process. These may include, but are not limited to:

Serum cytokines and inflammatory markers
Molecular skin biomarkers (inflammatory and barrier)
Circulating and tissue resident cellular phenotyping
Epidermal thickness and barrier markers from skin biopsies
Other biomarkers related autoimmune or inflammatory diseases Results:

FIG. 7A is a graph of the % of subjects to achieve EASI50 over time (Day 1 to Day 29) for a placebo and Compound 1 in the doses of 20 mg, 40 mg and 80 mg. FIG. 7B is a graph of the % of subjects to achieve EASI75 over time (Day 1 to Day 29) for a placebo and Compound 1 in the doses of 20 mg, 40 mg and 80 mg. 3 subjects reached EASI90, 2 subjects with 100% clearance. FIGS. 8A-8C shows the improvement in EASI, IGA & BSA after 4 weeks for a placebo, and Compound 1 in the doses of 20 mg, 40 mg and 80 mg. FIG. 8A is a graph of the % CFB (percentage change from baseline) for EASI (decrease) for the placebo and Compound 1 in the doses of 20 mg, 40 mg and 80 mg. FIG. 8B is a graph of the % CFB for BSA (body surface area) (decrease) for the placebo and Compound 1 in the doses of 20 mg, 40 mg and 80 mg. FIG. 8C is a graph of the % CFB for IGA 0-1 (Investigator's Global Assessment) for the placebo and Compound 1 in the doses of 20 mg, 40 mg and 80 mg. FIG. 9 is a graph of day 15 plasma concentration for Compound 1 in the doses of 20 mg, 40 mg and 80 mg. FIG. 9 shows dose-dependent $C_{max}$ and AUC, rapid oral absorption (Tmax 2-4 hrs) and moderate rate of elimination, $T_{1/2}$ of 10-14 hrs, and low inter- and intra-individual variability. FIG. 10 is a chart showing the inhibition of JAK and Syk kinase activity by Compound 1, Tofacitinib, Upadacitinib, and Baricitinib. In FIG. 10, the $IC_{50}$ values were determined in biochemical kinase assays using purified partial or full length enzymes. FIG. 11 is a chart showing inhibition of Compound 1 in JAK/STAT pathway in T cells stimulated with various cytokines. As shown in FIG. 11, Compound 1 showed strong inhibition of JAK/STAT pathway in T cells (primary) stimulated by various cytokines.

Figure 12:
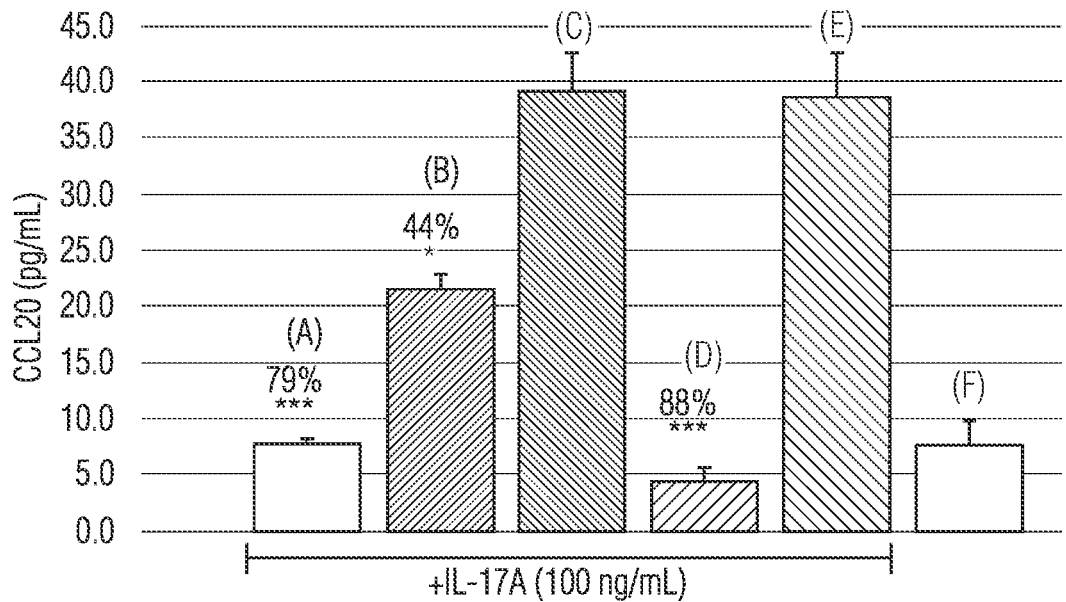
FIG. 12 is a chart showing Compound 1's inhibition of IL17 mediated CCL20 release in keratinocytes, as demonstrated in Example 3.
Figure 13:
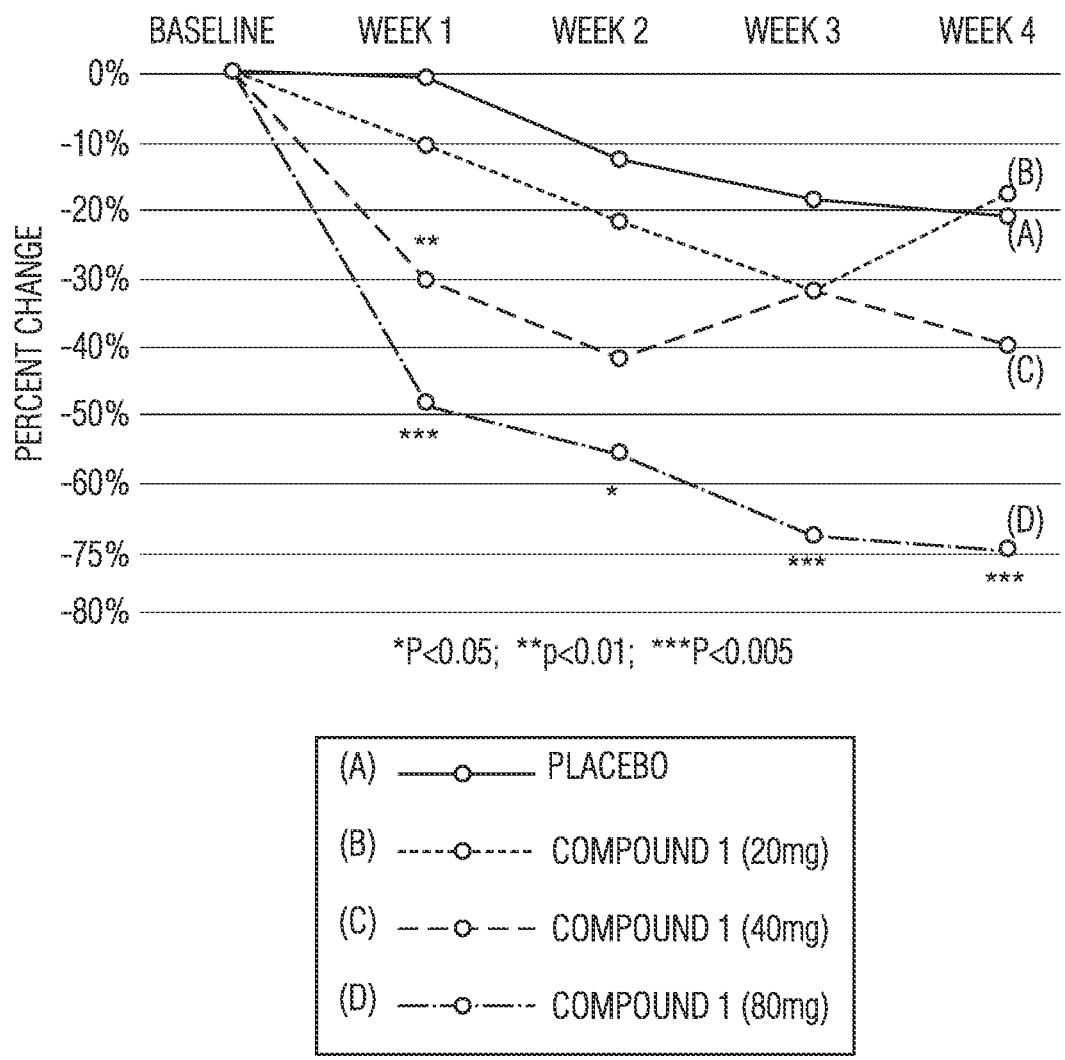
FIG. 13 is a graph showing average weekly change in pruritus (NRS) for a placebo, and Compound 1 in the doses of 20 mg, 40 mg and 80 mg, as demonstrated in Example 3.

FIG. 12 is a chart showing Compound 1's inhibition of IL17 mediated CCL20 release in keratinocytes. As shown in FIG. 12, unlike Tamatinib and Tofacitinib, Compound 1 inhibits IL-17-SYK mediated CCL20 release, from human keratinocytes, at levels similar to IL17 neutralizing antibodies (*p<0.05; *** p<0.001 compared to IL17+DMSO control (One-way ANOVA with Dunnett's multiple comparison test), and % is percent decrease from IL17+DMSO control). In FIG. 12, each bar represents mean and SEM for 3 replicates (n=3) of a single donor. FIG. 13 is a graph showing average weekly change in pruritus (NRS) for a placebo, and Compound 1 in the doses of 20 mg, 40 mg and 80 mg. As demonstrated in FIG. 13, Compound 1 shows early decrease in pruritis.

Figure 14A:
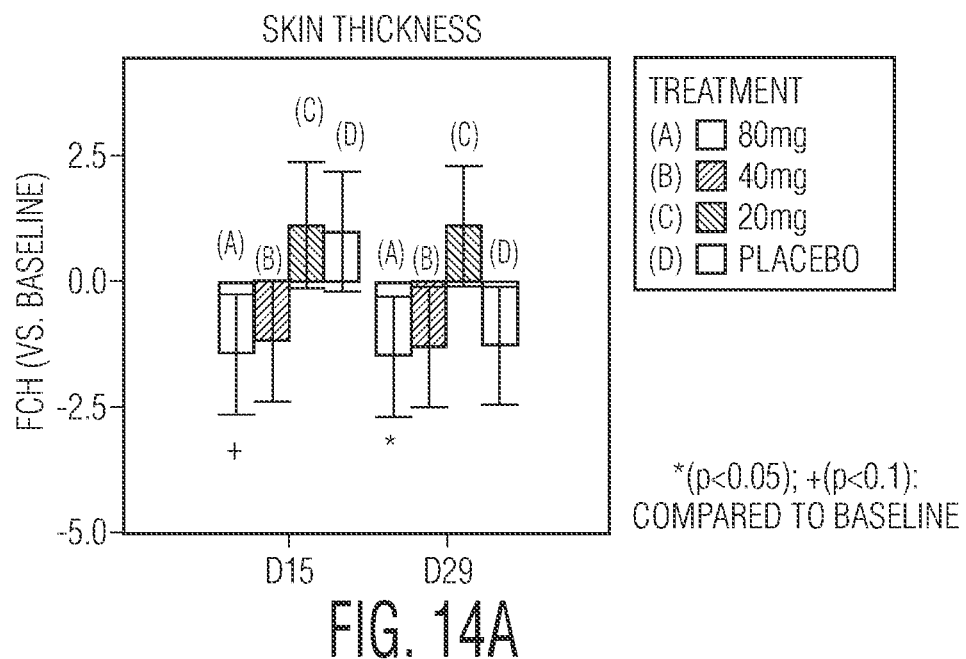
FIG. 14A is a graph showing improvement in skin thickness for Compound 1 in the doses of 20 mg, 40 mg and 80 mg.
Figure 14B:
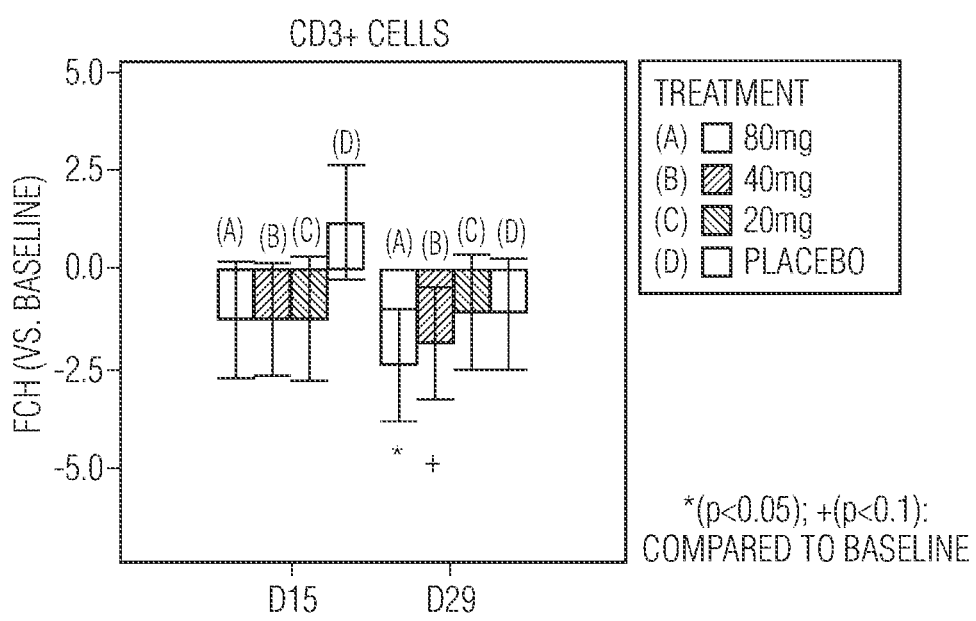
FIG. 14B is a graph showing improvement in CD3+ cells for Compound 1 in the doses of 20 mg, 40 mg and 80 mg.
Figures 14C, 15:
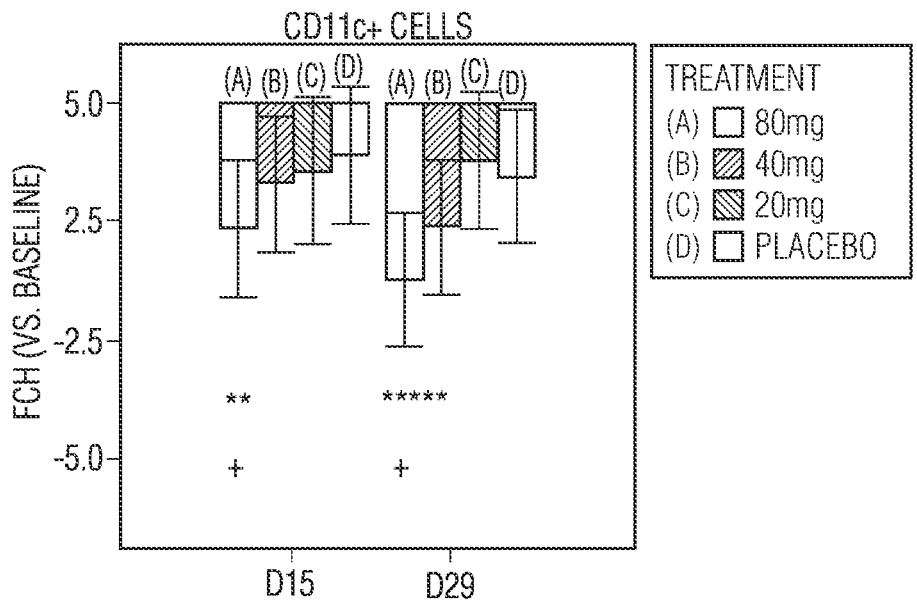
FIG. 14C is a graph showing improvement in CDT1c+ cells for Compound 1 in the doses of 20 mg, 40 mg and 80 mg.
FIG. 15 is a chart showing Treatment-Emergent Adverse Events (TEAE), as demonstrated in Example 3.
Figure 16B:
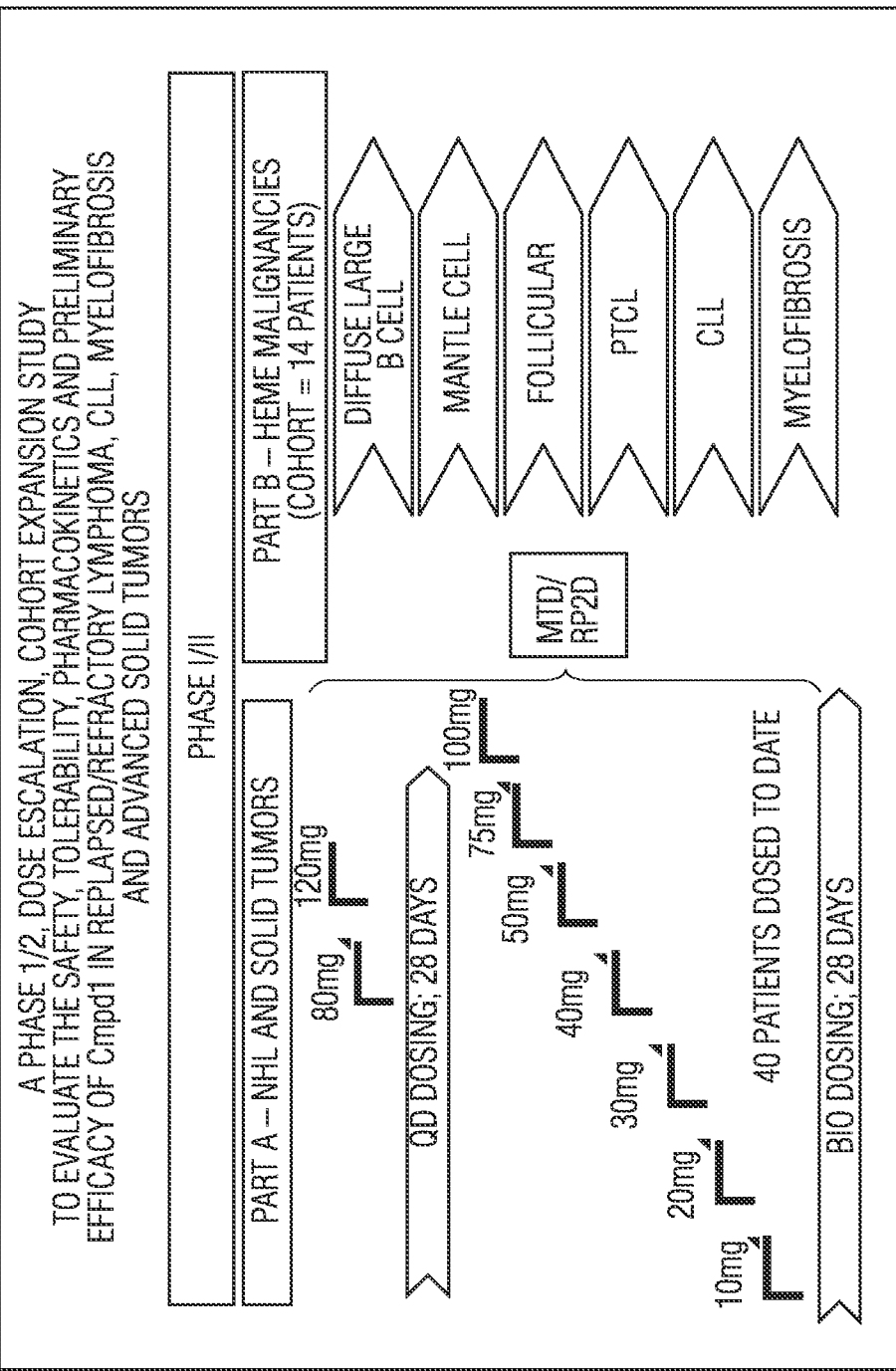
Figure 16D:
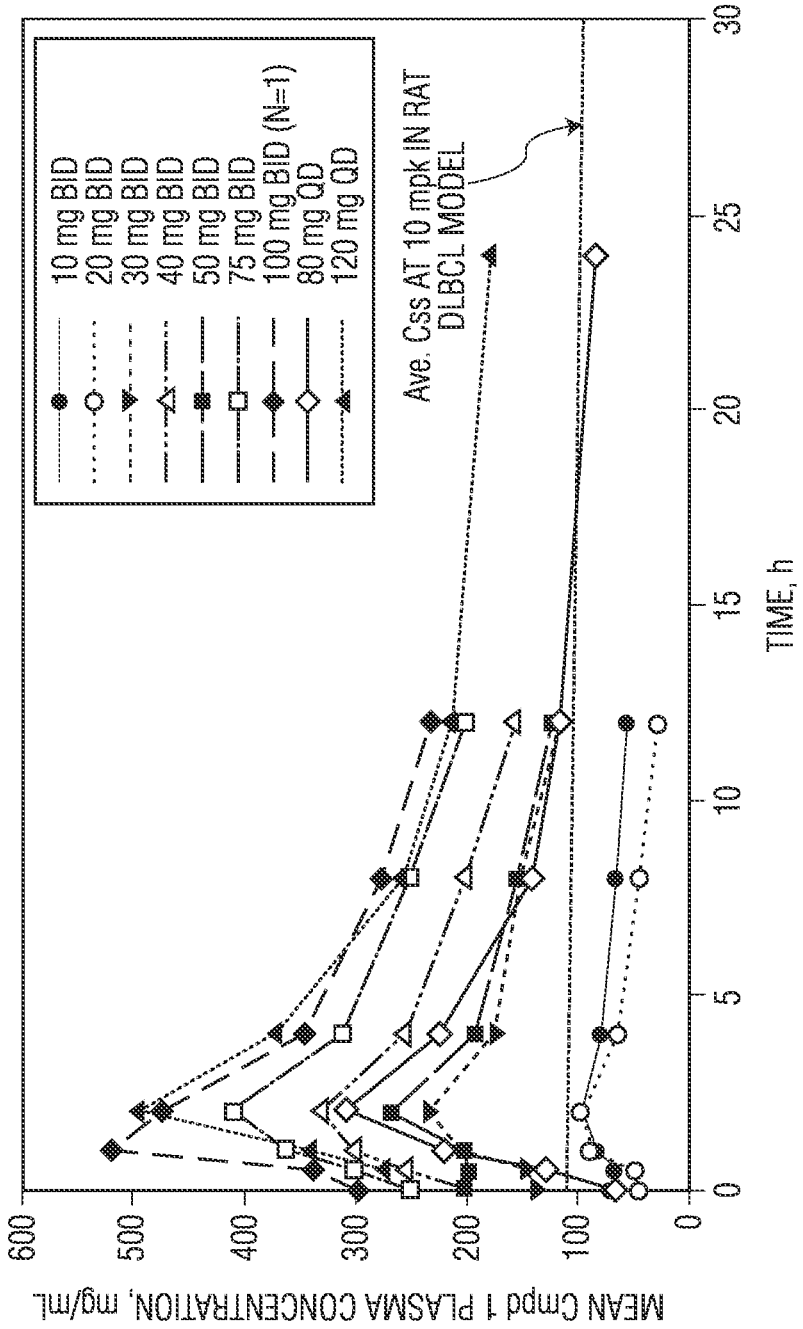
Figure 16E:
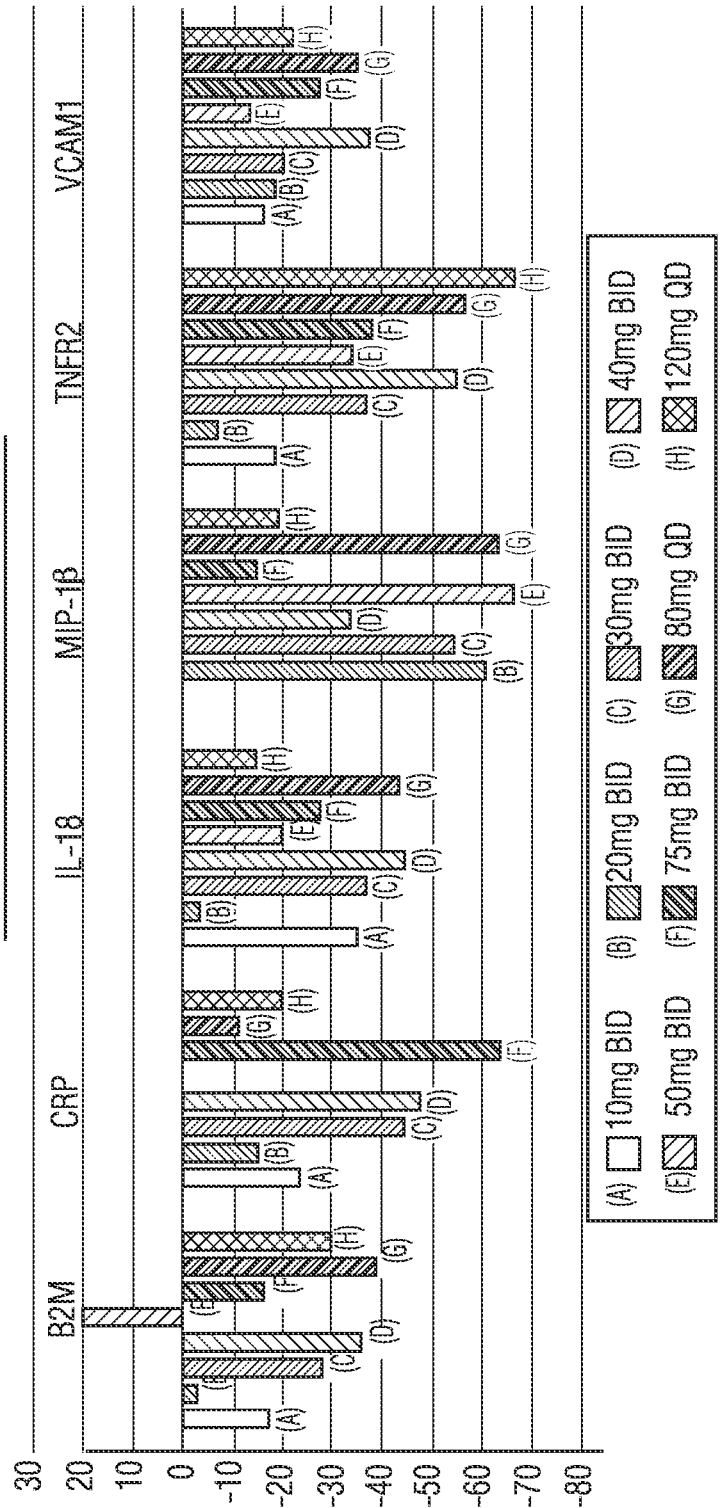
Figure 6F:
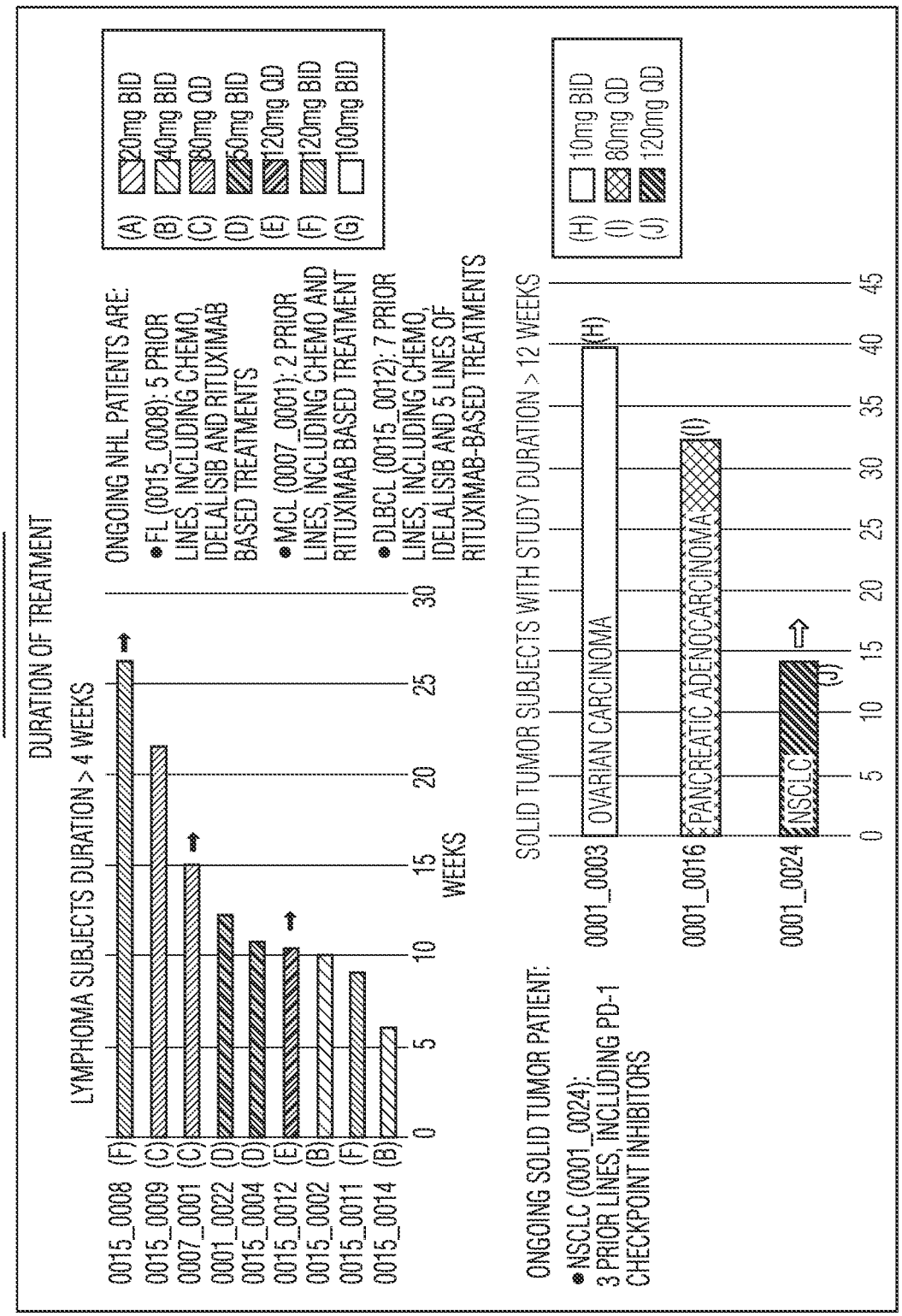

FIGS. 14A-C are graphs showing improvements in epidermal hyperplasia and cellular infiltrates observed as early as Day 15 for Compound 1 in the doses of 20 mg, 40 mg and 80 mg. FIG. 14A is a graph showing improvement in skin thickness for Compound 1 in the doses of 20 mg, 40 mg and 80 mg. Reductions in total skin thickness can be observed as early as Day 15. FIG. 14B is a graph showing improvement in CD3+ cells for Compound 1 in the doses of 20 mg, 40 mg and 80 mg. T cell infiltration into all layers of the skin is reduced with 40 and 80 mg ASN002 at Day 29. FIG. 14C is a graph showing improvement in CD11c+ cells for Compound 1 in the doses of 20 mg, 40 mg and 80 mg. Myeloid DC infiltration into all layers of the skin is reduced with 40 and 80 mg ASN002 as early as Day 15. FIG. 15 is a chart showing Treatment-Emergent Adverse Events (TEAE), as demonstrated in Example 3.

Conclusion:

Compound 1 showed clear efficacy in moderate to severe AD patients. Compound 1 results in rapid symptom improvement—significant reduction in patient reported itch was observed as early as 2nd day of treatment with Compound 1. Compound 1 was well tolerated in patients with moderate to severe atopic dermatitis. Compound 1 once daily demonstrated predictable pharmacokinetics as evidenced by dose-dependent exposure, minimum individual variability and accumulation. Compound 1 treatment down regulates inflammatory pathways, showing improvements in epidermal hyperplasia and cellular infiltrates as early as Day 15.

The most common adverse events were headache and nausea predominantly reported on Day 1 associated with fasting and also reported from placebo patients. No serious infections or thromboembolic events occurred. No clinically significant changes in chemistry lab parameters except asymptomatic, mild-to-moderate transient elevations of CPK were observed. No changes in lipid profile were observed. No clinically significant changes in hematologic lab parameters including platelets, neutrophils and lymphocytes were observed. Subjects in the Compound 1 treatment arms showed rapid onset and dose-related declines after 4 weeks in EASI50 of 29%, 100% and 88% and EASI75 of 0%, 63% and 50% for the 20, 40 and 80 mg cohorts respectively. Baseline EASI scores were 29.0, 21.3 and 29.0, respectively. The average decreases in EASI and in Pruritus Numeric Rating Scale (NRS) at week 4 for the 20, 40 and 80 mg cohorts were 21%, 79% and 70% and 15%, 47% and 71% respectively. In the 80 mg cohort, reduction in itch was seen as early as Day 2, (~45%) and improvements were also observed in the 40 and 80 mg cohorts in IGA assessments (up to 38% reaching 0-1). These clinical improvements were also associated with reversal of cutaneous biomarkers (cellular infiltrates, immune and hyperplasia markers) particularly in the mid and high dose.

Abstract for Example 3

Background: Dysregulation of Th2 and Th22 cytokine pathways are implicated in the pathogenesis of atopic dermatitis (AD). Compound 1 is a novel oral inhibitor of JAK and SYK signaling (including Tyk2), that diminishes production of Th2 and Th22 cytokines. Syk also regulates IL17R signaling in keratinocytes and keratinocyte differentiation. Objectives: Efficacy, Safety and Pharmacology of Compound 1 was evaluated in moderate-to-severe AD patients in a Phase 1b randomized, double-blind, placebo-controlled study (NCT03139981).

Methods: Patients were randomized 1:3 placebo or Compound 1 at 20, 40 or 80 mg once daily for 4 weeks (n=36). Inclusion criteria were Eczema Area and Severity Index (EASI) ≥16, body surface area (BSA) involvement ≥10% and an Investigator's Global Assessment (IGA) of ≥3 at baseline visit. Study objectives included safety/tolerability, efficacy and pharmacokinetic measurements. No concomitant administration of topical corticosteroids or other immunosuppressants was permitted during or prior to study.

Results: Compound 1 was very well tolerated at all dose levels. The most common adverse events were transient, mild headache and nausea, mostly restricted to Day 1 of dosing. Subjects in the Compound 1 treatment arms showed rapid onset and dose-related declines after 4 weeks in EASI50 of 29%, 100% and 88% and EASI75 of 0%, 63% and 50% for the 20, 40 and 80 mg cohorts respectively. Baseline EASI scores were 29.0, 21.3 and 29.0, respectively. The average decreases in EASI and in Itch Numeric Rating Scale (NRS) at week 4 for the 20, 40 and 80 mg cohorts were 21%, 79% and 70% and 15%, 47% and 71% respectively. In the 80 mg cohort, reduction in itch was seen as early as Day 2, (~45%) and improvements were also observed in the 40 and 80 mg cohorts in IGA assessments (up to 38% reaching 0-1). These clinical improvements were also associated with reversal of cutaneous biomarkers (cellular infiltrates, immune and hyperplasia markers) particularly in the mid and high dose.

Conclusion: This is a clinical report on safety, efficacy and effect on the pathologic lesional skin phenotype with oral JAK/SYK inhibitor Compound 1 in moderate-to-severe AD. Compound 1 was very well tolerated and demonstrated early improvements in pruritus and robust activity in EASI after 4 weeks with associated reversal of cutaneous biomarkers of inflammation.

Example 4

Clinical Activity, Safety and Tolerability of Compound 1, a Dual SYK/JAK Inhibitor, Inpatients with Non-Hodgkin's Lymphoma (NHL)

A formulation of the disclosure comprising 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile comprises a potent inhibitor of Spleen Tyrosine Kinase (SYK) and Janus Kinases (JAK). Pre-clinical studies indicate that the formulation has low nM IC50s against SYK and JAK, decreases proliferation in ibrutinib-resistant cell lines, and suppresses tumor growth in rodent xenograft models of NHL and other hematologic malignancies.

Methods: Phase 1/2 clinical trial in patients with solid tumors and hematologic malignancies evaluates escalating oral doses of the formulation disclosed herein at 10, 20, 30, 40, 50, 75 and 100 mg BID and 80 and 120 mg QD mg (NCT02440685). Phase 1 allows patients with solid tumors or hematologic malignancies; Phase 2 allows only patients with diffuse large B-Cell lymphoma (DLBCL), follicular lymphoma (FL) or mantle cell lymphoma (MCL). Endpoints include safety, tolerability, pharmacokinetics, serum markers of inflammation, and response using RECIST or Lugano Classification System, Results: Thirty-eight patients have enrolled in the DLT phase at doses of 10 mg-100 mg BID and at 80-120 mg QD. All patients had multiple prior lines of treatment (range: 2-8). The present formulation was well tolerated. No dose limiting adverse events have been reported at these dose levels. Most drug-related adverse events were Gr 1/2 (e.g.

headache, fatigue). Steady-state systemic exposure was high ($C_{max}$, AUC (0-12 h) and $T_{1/2}$ at 40 mg BID were 0.7 µM, 6.3 µM·h and 18 h, respectively). High systemic exposure was also observed at 80 mg QD. Robust reduction of CRP, IL-18, MIP1β, VCAM-1, TNFR2 was observed at all doses. About 50% reduction in target lesions at 3 months in a FL patient (Lugano, 6 prior lines) and stable disease and reduction of pruritus in a peripheral T-Cell lymphoma patient after 2 months (Lugano, 2 prior lines) of treatment were observed. Treatment using the present formulation continues in both lymphoma patients. Formulation-induced lymphocytosis, indicative of recompartmentalization, has been observed in two recently enrolled patients. Accrual of patients continues. FIGS. 16A-16G provide clinical activity, safety and tolerability data for formulations of the present disclosure.

Conclusion: The present formulation was safe and well tolerated. Encouraging preliminary evidence of efficacy in NHL patients was observed. MTD has not been reached and dose escalation continues.

While the present disclosure has been discussed in terms of certain embodiments, it should be appreciated that the present disclosure is not so limited. The embodiments are explained herein by way of example, and there are numerous modifications, variations and other embodiments that can be employed that would still be within the scope of the present disclosure.

The invention claimed is:

1. A pharmaceutical formulation comprising granules, wherein the granules comprise:
   (i) a micronized compound that is 2-(1-(4-((4-(4-hydroxypiperidin -1-yl)phenyl)amino)-5-oxo-5,6-dihydropyrimido[4,5-d]pyridazin-2-yl)piperidin-4-yl)acetonitrile in an amount that is about 20 mg to 80 mg, or a pharmaceutically acceptable salt thereof;
   (ii) hydroxypropyl cellulose; and
   about 1 mg to 20 mg croscarmellose sodium;
   wherein the formulation further comprises one or more extragranular components; and wherein the one or more extragranular components comprise sodium lauryl sulfate.

2. The pharmaceutical formulation of claim 1, further comprising one or more antioxidants.

3. The pharmaceutical formulation of claim 2, wherein the one or more antioxidants comprise at least one of vitamin E or butylated hydroxytoluene.

4. The pharmaceutical formulation of claim 3, wherein the one or more antioxidants is vitamin E.

5. The pharmaceutical formulation of claim 1, further comprising one or more fillers.

6. The pharmaceutical formulation of claim 5, wherein the one or more fillers comprises lactose monohydrate.

7. The pharmaceutical formulation of claim 1, wherein the extragranular components comprise at least one of: (a) one or more tableting fillers; (b) one or more disintegrants; (c) one or more lubricants; or (d) one or more surfactants.

8. The pharmaceutical formulation of claim 1, wherein the extragranular components comprise at least one of: (a) one or more tableting fillers comprising microcrystalline cellulose; (b) one or more disintegrants comprising croscarmellose sodium; (c) or one or more lubricants comprising magnesium stearate.

9. The pharmaceutical formulation of claim 1, wherein the compound is 2-(1-(4-((4-(4-hydroxypiperidin-1-yl)phenyl)amino) -5-oxo-5, 6-dihydropyrimido[4,5-d]pyridazin-2-yl)piperidin-4-yl)acetonitrile hydrochloride.

10. The pharmaceutical formulation of claim 1, wherein the pharmaceutical formulation comprises about 20 mg, about 40 mg, or about 80 mg of the compound, calculated as a free base.

11. The pharmaceutical formulation of claim 10, wherein the pharmaceutical formulation comprises about 40 mg of the compound, calculated as a free base.

12. The pharmaceutical formulation of claim 10, wherein the pharmaceutical formulation comprises about 80 mg of the compound, calculated as a free base.

13. The pharmaceutical formulation of claim 1, wherein the granules have a particle size of less than about 20 microns.

14. The pharmaceutical formulation of claim 1, wherein the pharmaceutical formulation is a tablet.

15. The pharmaceutical formulation of claim 14, wherein the tablet is coated.

16. The pharmaceutical formulation of claim 1, comprising granules, wherein the granules comprise:
   (i) a micronized compound that is 2-(1-(4-((4-(4-hydroxypiperidin-1-yl)phenyl)amino) -5-oxo-5,6-dihydropyrimido[4,5-d]pyridazin-2-yl)piperidin-4-yl)acetonitrile in an amount that is about 20 mg to 80 mg, or a pharmaceutically acceptable salt thereof;
   (ii) hydroxypropyl cellulose;
   (iii) about 1 mg to 20 mg croscarmellose sodium;
   (iv) vitamin E; and
   (v) lactose monohydrate.

17. The pharmaceutical formulation of claim 16, wherein the compound is 2-(1-(4-((4-(4-hydroxypiperidin-1-yl)phenyl)amino) -5-oxo-5,6-dihydropyrimido[4,5-d]pyridazin-2-yl)piperidin-4-yl)acetonitrile hydrochloride.

18. The pharmaceutical formulation of claim 16, wherein the pharmaceutical formulation comprises about 20 mg, about 40 mg, or about 80 mg of the compound, calculated as a free base.

19. The pharmaceutical formulation of claim 18, wherein the pharmaceutical formulation comprises about 40 mg of the compound, calculated as a free base.

20. The pharmaceutical formulation of claim 18, wherein the pharmaceutical formulation comprises about 80 mg of the compound, calculated as a free base.

21. The pharmaceutical formulation of claim 16, wherein the extragranular components comprise microcrystalline cellulose, croscarmellose sodium, and magnesium stearate.

22. A kit comprising:
   one or more dosage forms comprising the pharmaceutical formulation of claim 1; and
   instructions for administering the one or more dosage forms to a subject suffering from an inflammatory disorder.

23. A method of treating an inflammatory disorder or autoimmune disease, comprising administering to a subject in need thereof the pharmaceutical formulation of claim 1.

24. The method of claim 23, wherein the inflammatory disorder or autoimmune disease is selected from atopic dermatitis, alopecia areata, hand and foot eczema, hidradenitis suppurativa, pemphigus vulgaris, psoriasis, cutaneous lupus, vitiligo, inflammatory bowel disease, rheumatoid arthritis, asthma, allergic rhinitis, systemic lupus erythematosus, psoriatic arthritis, and multiple sclerosis.

25. The method of claim 23, wherein the inflammatory disorder is hand and foot eczema.

26. A method of preparing a tablet formulation, the method comprising:

(A) providing intragranular ingredients comprising
  (i) a micronized compound that is 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile, or a pharmaceutically acceptable salt thereof; and
  (ii) croscarmellose sodium;
(B) granulating the intragranular ingredients while adding a 10% w/w solution of one or more binders comprising hydroxypropyl cellulose in 99% v/v isopropyl alcohol until granules are formed;
(C) drying and milling the granules to make micronized granules;
(D) mixing the micronized granules with one or more extragranular components; and
(E) compressing the micronized granules and the one or more extragranular components into a tablet, thereby providing the tablet formulation;
wherein the one or more extragranular components comprise sodium lauryl sulfate.

* * * * *